US012178512B2

(12) United States Patent
Fehr et al.

(10) Patent No.: US 12,178,512 B2
(45) Date of Patent: Dec. 31, 2024

(54) IMPLANTABLE DEVICES WITH EMBEDDED PRESSURE SENSORS

(71) Applicant: Qura, Inc., Duxbury, MA (US)

(72) Inventors: Jean-Noel Fehr, Neuchatel (CH); Stefan Bauer, Helbling (CH); Alain Saurer, Helbling (CH); Douglas P. Adams, Sudbury, MA (US); Amitava Gupta, Roanoke, VA (US)

(73) Assignee: Qura, Inc., Duxbury, MA (US)

( * ) Notice: Subject to any disclaimer, the term of this patent is extended or adjusted under 35 U.S.C. 154(b) by 1107 days.

(21) Appl. No.: 17/066,564

(22) Filed: Oct. 9, 2020

(65) Prior Publication Data

US 2021/0137379 A1 May 13, 2021

Related U.S. Application Data

(63) Continuation-in-part of application No. PCT/US2018/056277, filed on Oct. 17, 2018.
(Continued)

(51) Int. Cl.
*A61B 3/16* (2006.01)
*A61F 2/16* (2006.01)
(Continued)

(52) U.S. Cl.
CPC .............. *A61B 3/16* (2013.01); *A61F 2/1613* (2013.01); *A61L 27/18* (2013.01); *A61L 27/34* (2013.01);
(Continued)

(58) Field of Classification Search
CPC .............. A61B 3/16; A61B 2562/0214; A61B 2562/0247; A61F 2/1613;
(Continued)

(56) References Cited

U.S. PATENT DOCUMENTS 6,796,942 B1    9/2004  Kreiner et al.
6,939,299 B1 *  9/2005  Petersen ................... A61B 3/16
                                                     600/587
(Continued)

FOREIGN PATENT DOCUMENTS

WO       2006067638 A2      6/2006
WO   WO-2012157623 A1 * 11/2012 ........... A61F 2/1613
(Continued)

OTHER PUBLICATIONS

Biros et al., "Development of glaucoma after cataract surgery in dogs", in J Am Vet Med Assoc., 2000; 216(11), pp. 1780. 7 pages.
(Continued)

*Primary Examiner* — Javier G Blanco
(74) *Attorney, Agent, or Firm* — Smith Baluch LLP

(57) ABSTRACT

Implantable pressure sensors and implantable electronics should be packaged in hermetically sealed modules with biocompatible surfaces before being implanted. Packaging designs should be compact and cause little to no interference with the mechanical (and optical) properties or functions of the implant. For a pressure sensor in an intraocular lens, this means that the sensor and packaging should allow the lens to be folded so that it can be implanted through a small incision in the eye. An inventive implantable pressure sensor is coated with a silicone elastomer and hermetically sealed by a multilayer coating of $SiO_x$ and Parylene C, which may also encapsulate other components, including a microcontroller or processor, rechargeable batteries, sensors, resistors, capacitors, wireless transceivers, and/or antennas mounted on a transparent substrate. This combination of silicone gel and multilayer coating isolates the pressure sensor from surrounding tissue while allowing the pressure sensor to measure pressure precisely and quickly.

11 Claims, 18 Drawing Sheets

Related U.S. Application Data

(60) Provisional application No. 62/912,827, filed on Oct. 9, 2019.

(51) Int. Cl.
    *A61L 27/18* (2006.01)
    *A61L 27/34* (2006.01)
    *B05D 7/00* (2006.01)

(52) U.S. Cl.
    CPC ........ *B05D 7/58* (2013.01); *A61B 2562/0214* (2013.01); *A61F 2002/1689* (2013.01); *A61F 2002/169053* (2015.04); *A61F 2210/0076* (2013.01); *A61F 2240/001* (2013.01); *A61F 2250/0001* (2013.01); *A61F 2250/0096* (2013.01); *A61L 2420/02* (2013.01); *A61L 2420/08* (2013.01); *A61L 2430/16* (2013.01)

(58) Field of Classification Search
    CPC .. A61F 2002/1689; A61F 2002/169053; A61F 2210/0076; A61F 2240/001; A61F 2250/0001; A61F 2250/0096; A61F 2/16; A61F 2002/1699; A61F 2002/7635; A61L 27/18; A61L 27/34; A61L 2420/02; A61L 2420/08; A61L 2430/16; B05D 7/58; B05D 2518/12; B05D 7/57; B05D 2505/50
    See application file for complete search history.

(56) References Cited

U.S. PATENT DOCUMENTS

| | | | |
|---|---|---|---|
| 8,313,811 B2 | 11/2012 | Hogg et al. | |
| 8,313,819 B2 * | 11/2012 | Hogg | H05K 3/284 |
| | | | 361/752 |
| 8,361,591 B2 | 1/2013 | Hogg et al. | |
| 8,475,374 B2 | 7/2013 | Irazoqui et al. | |
| 9,078,613 B2 | 7/2015 | Irazoqui et al. | |
| 9,173,564 B2 | 11/2015 | Choo et al. | |
| 9,596,988 B2 | 3/2017 | Irazoqui et al. | |
| 9,662,021 B2 | 5/2017 | Chow et al. | |
| 10,044,227 B2 | 8/2018 | Chappell et al. | |
| 10,426,341 B2 | 10/2019 | Choo et al. | |
| 2009/0143761 A1 * | 6/2009 | Cantor | A61N 1/0444 |
| | | | 604/501 |
| 2010/0137694 A1 | 6/2010 | Irazoqui et al. | |
| 2012/0238857 A1 | 9/2012 | Wong et al. | |
| 2013/0184554 A1 * | 7/2013 | Elsheikh | A61B 3/16 |
| | | | 600/398 |
| 2013/0226293 A1 * | 8/2013 | Venkateswaran | A61F 2/1627 |
| | | | 623/6.37 |
| 2013/0308093 A1 * | 11/2013 | Qiu | C09D 5/1637 |
| | | | 351/159.33 |
| 2013/0330498 A1 * | 12/2013 | Hogg | H05K 3/284 |
| | | | 427/2.24 |
| 2016/0324628 A1 | 11/2016 | Gupta et al. | |
| 2017/0020660 A1 | 1/2017 | Hyde et al. | |
| 2017/0164831 A1 | 6/2017 | Choo et al. | |
| 2017/0209045 A1 | 7/2017 | Choo et al. | |
| 2018/0035888 A1 | 2/2018 | Irazoqui et al. | |
| 2018/0375382 A1 | 12/2018 | Chappell et al. | |
| 2019/0175015 A1 | 6/2019 | Adams et al. | |
| 2020/0237218 A1 | 7/2020 | Irazoqui et al. | |

FOREIGN PATENT DOCUMENTS

| | | |
|---|---|---|
| WO | 2013090886 A1 | 6/2013 |
| WO | 2019164940 A1 | 8/2019 |
| WO | 2019191748 A1 | 10/2019 |
| WO | 2019216945 A1 | 11/2019 |
| WO | 2020023036 A1 | 1/2020 |
| WO | 2020046299 A1 | 3/2020 |
| WO | 2020160262 A1 | 8/2020 |
| WO | 2020236139 A1 | 11/2020 |

OTHER PUBLICATIONS

Cook et al., "Canine cataract surgery." Cataract & Refractive Surgery Today (2008): 32-34.

Gellat et al., "Prevalence of the breed-related glaucomas in purebred dogs in North America." Veterinary ophthalmology 7.2 (2004): 97-111.

Hogg et al., "Protective multilayer packaging for long-term implantable medical devices." Surface and Coatings Technology 255 (2014): 124-129.

Hogg et al., "Ultra-thin layer packaging for implantable electronic devices." Journal of Micromechanics and Microengineering 23.7 (2013): 075001. 13 pages.

Hogg, "Development and Characterization of Ultrathin Layer Packaging for Implantable Medical Devices," Ph.D. thesis He-Arc ingénierie, 2014. 219 pages.

International Search Report and Written Opinion in International Application No. PCT/US2018/056277 mailed Dec. 21, 2018, 10 pages.

Kung et al., "Cataract surgery in the glaucoma patient." Middle East African journal of ophthalmology 22.1 (2015): 10. 12 pages.

* cited by examiner

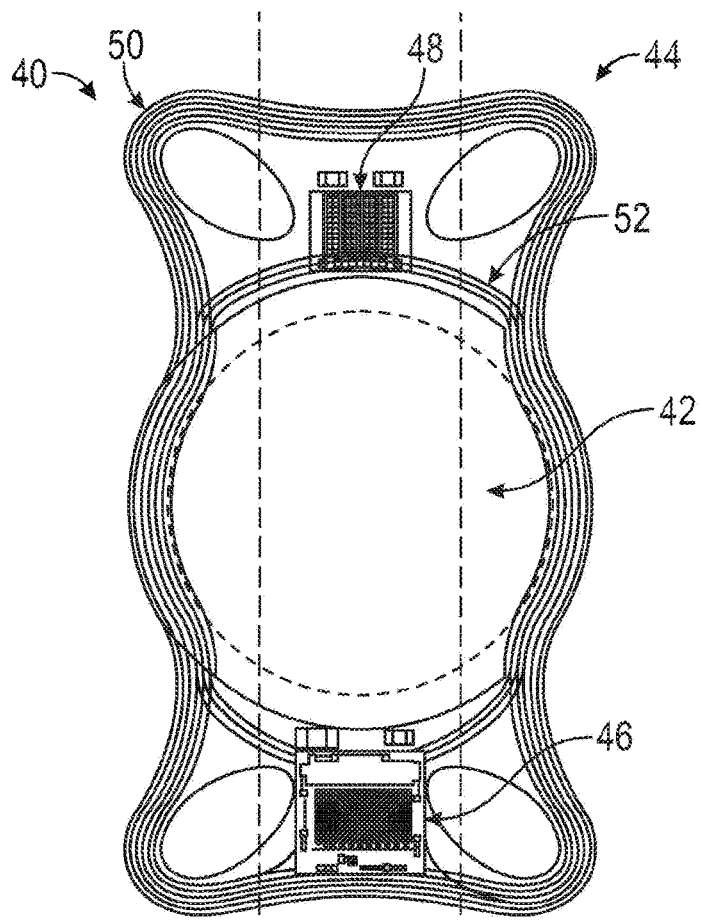
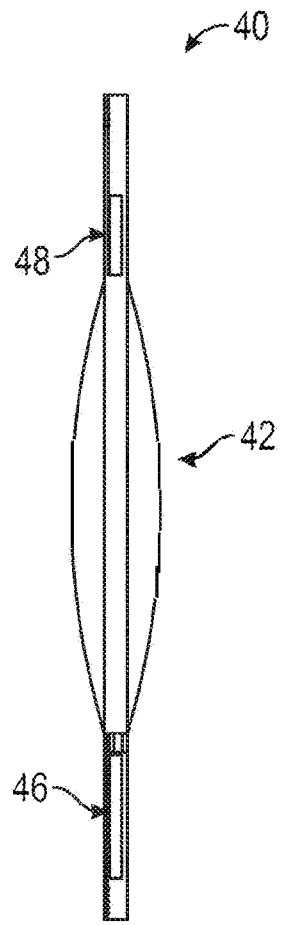
FIG. 4A
FIG. 4B
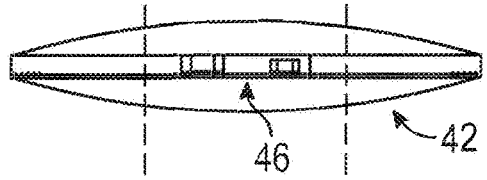
FIG. 4C
| Biocompatible Coating (Optional) | 801 |
| Multilayer Barrier Coating | 831 |
| Gel (Optional) | 832 |
| Sensor | 850 |
| IOL | 800 |
FIG. 8

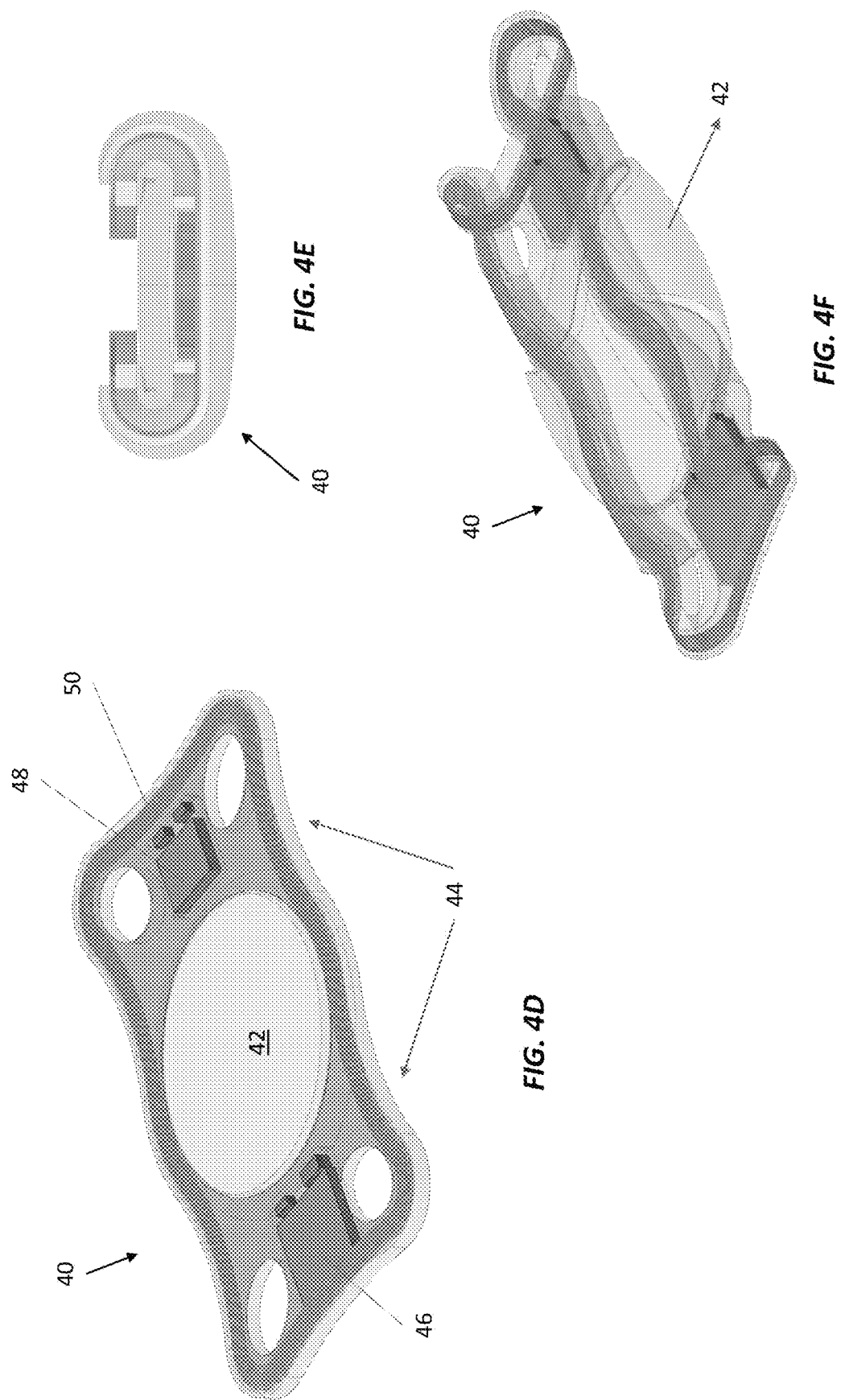

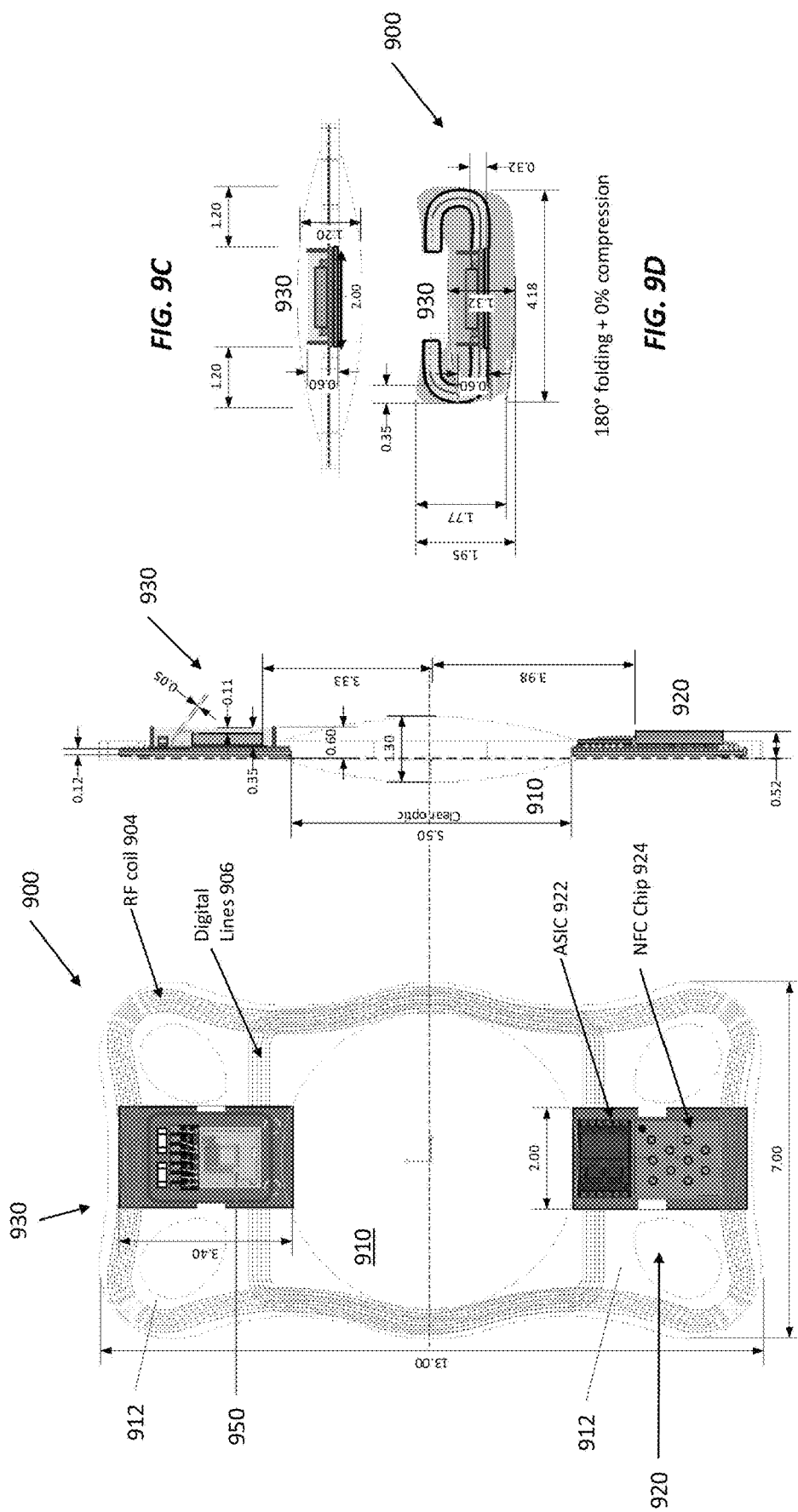

| Material | Water absorption (%) | 24h/23°C Water absorption (%) | Hardness/Elastic modulus (Shore/MPa) | CTE (10^-6 /K) | Dielectric constant 100Hz - 10MHz | Volume Resistivity (Ohm-cm) | Uncured Viscosity @ RT (cP) | ETO sterilization ok? | Curing Temp/time (°C/hrs) |
|---|---|---|---|---|---|---|---|---|---|
| Silastic MDX4 4210 mix Ratio 2:1 (Reference) | 0.4 | ~0.1 | 0.1/500 | -59 to 79 | 3.0-3.0 | 2E15 | 60'000-110'000 | ✓ | RT 24h to 100°C/15min |
| MED-6655 Nusil RTV Fluorosilicone | 0 | 0 | 35/3600 | ~81 | 6.95-7.35* | 1E13* | 700 | | RT/ 72 hrs |
| MED-6381 Nusil RTV gel (unfilled) | ~0.4 | ~0.1 | 3/1700 | ~59 to 79 | 2.5-2.77* | 1E15* | | | RT 24 hrs |
| MED-6-6606 Nusil RTV dispersion | TBC | ~0.1 | 3/2200 | ~59 to 79 | 2.5-2.77* | 1E15* | 95 | | RT/72hrs |
| MED-6605 Nusil RTV dispersion | TBC | ~0.1 | 3/2600 | ~59 to 79 | 2.5-2.77* | 1E15* | 700 | | RT/5 days |
| MED-6621 Nusil | TBC | ~0.1 | 2/2500 | ~59 to 79 | 2.5-2.77* | 1E15* | adjustable | | RT/30min or 75°C/45min |

* Implantable >30days with hardness <=25Shore A (TBC by FE simulation → in process) and curing temperature <=85°C, Water absorption at saturation <0.4%, Good adhesion to parylene and minimal adhesion to sensor casing, ETO sterilization compatible.

FIG. 9F

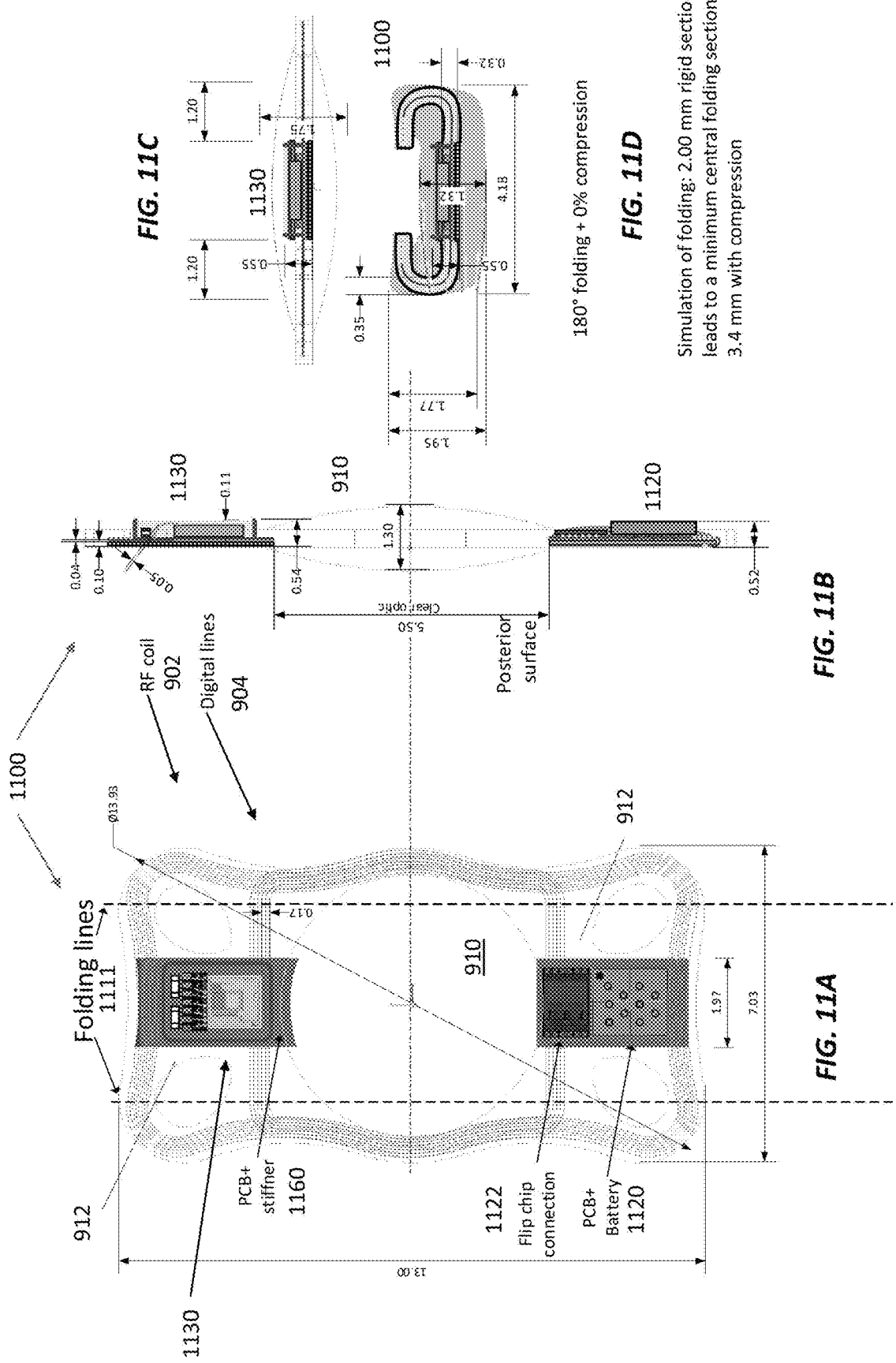

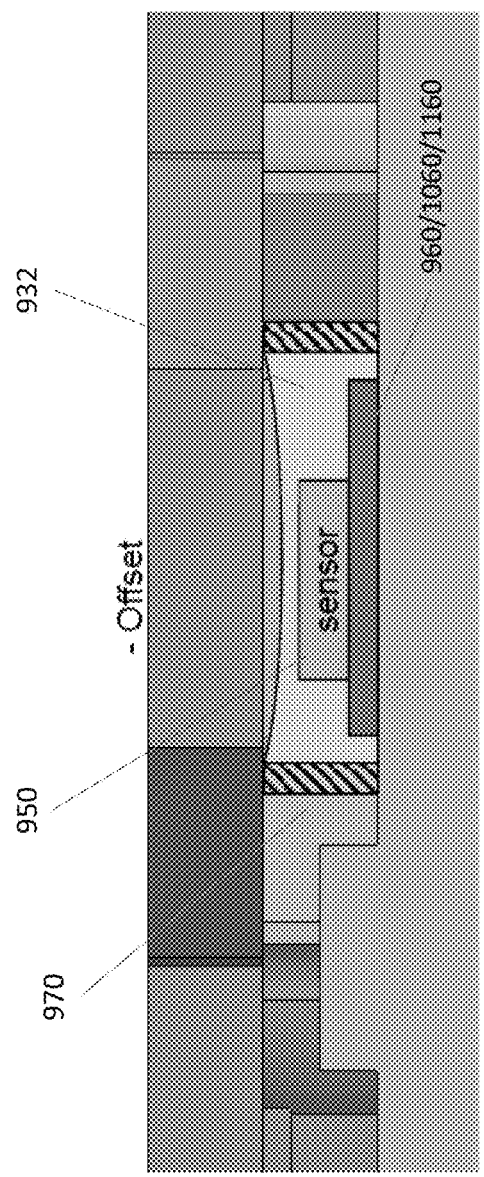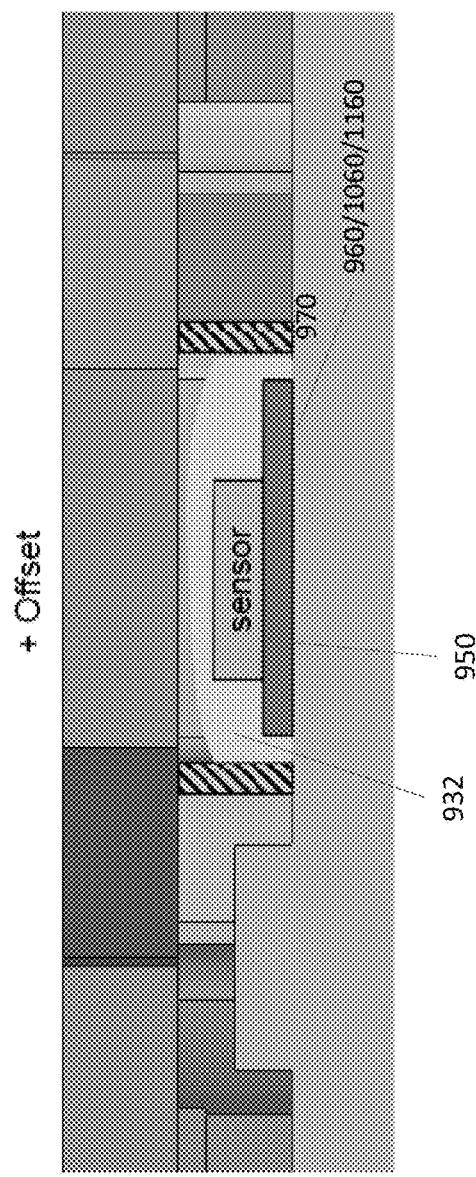

IMPLANTABLE DEVICES WITH EMBEDDED PRESSURE SENSORS

CROSS-REFERENCE TO RELATED APPLICATION(S)

This application claims the priority benefit, under 35 U.S.C. 119(e), of U.S. Application No. 62/912,827, which was filed on Oct. 9, 2019. This application is also a continuation-in-part of International Application No. PCT/US2018/056277, which designates the United States and was filed on Oct. 17, 2018. Each of these applications is herein incorporated by reference in its entirety for all purposes.

BACKGROUND

Intraocular lenses (IOLs) are typically permanent, plastic lenses that are surgically implanted inside of the eye to replace or supplement the eye's natural crystalline lens. They have been used in the United States since the late 1960s to restore vision to cataract patients, and more recently are being used in several types of refractive eye surgery.

The natural crystalline lens is a critical component of the complex optical system of the eye. The crystalline lens provides about 17 diopters of the total 60 diopters of the refractive power of a healthy human eye. An IOL used in cataract surgery may be folded and inserted through the same tiny opening that is used to remove the natural crystalline lens. Once in the eye, the IOL may unfold to its full size. The opening in the eye may be as small as 2.5 mm in length, so that it heals quickly without stitches. An IOL may be made of inert materials or may have a biocompatible coating that does not trigger a rejection response by the body.

Most IOLs are permanent. They rarely need replacement, except when the measurements of the eye before surgery have not accurately determined the required focusing power of the IOL. Also, the surgery itself may change the optical characteristics of the eye. Most IOLs implanted during cataract surgery are monofocal lenses. The optical power of the IOL is selected such that the eye is set for distance vision. Therefore, in most cases the patient will still require reading glasses after surgery. IOLs may be static multifocal lenses, which attempt to function more like the eye's natural lens by providing clear vision at a distance and reasonable focus for a range of near distances for patients with presbyopia.

A considerable number of patients that undergo cataract surgery have preexisting glaucoma. Glaucoma has been diagnosed in nearly 15% of the US population above age 80. The incidence of glaucoma rises with age and is more prevalent in the African American and Hispanic segments of the US population. Many of these patients develop cataract at an earlier age (typically between 50 and 75 years of age) and undergo cataract extraction and in virtually all cases implantation of an IOL. Many of these pseudophakes or aphakes, especially those with diabetes, may develop glaucoma, including angle closure glaucoma caused by postoperative inflammation.

A postoperative increase in intraocular pressure may be caused by residual viscoelastic gels left over after surgery, incursion of the vitreous caused by breach of the posterior capsule during cataract surgery, or iatrogenic damage to the iris, leading to pigment dispersion or the Ugh (uveitis-glaucoma-hyphema) syndrome. Moreover, a certain percentage of persons who develop glaucoma at a relatively early age subsequently develop cataracts and undergo cataract extraction and implantation of an IOL. Models based on UN world population projections suggest that 79.6 million persons will be afflicted with either open-angle glaucoma (OAG) or angle-closure glaucoma (ACG) by the year 2020, with 5.9 million and 5.3 million projected to be bilaterally blind from these two conditions, respectively. (Kung, J S, et al., "Cataract surgery in glaucoma patient" in *Middle East Afr J Ophthalmol,* 2015; 22(1), pp 10-17).

Recently, IOLs have been implanted in canines, mainly pet dogs, after cataract extraction. Commonly affected breeds include the American cocker spaniel, poodle, Boston terrier, miniature Schnauzer, Bichon Frise, and Labrador retriever. Typically, genetic lenticular opacities are bilateral and slowly progressive. Rapidly progressive cataracts commonly occur in dogs with diabetes mellitus. Secondary lens-induced uveitis is a frequent finding that may complicate pre- and postoperative management (Cook, C, "Canine Cataract Surgery", *Cataract & Refractive Surgery Today,* 2008; pp 32).

FIG. 1 shows an IOL 2 developed for implantation in a canine. This IOL 2 is a hydrophilic posterior chamber intraocular implant (PCL) developed for canines. TABLE 1 gives the dimensions of this IOL 2 and its intended site of implantation.

TABLE 1

Dimensions and other specifications of a posterior chamber intraocular lens (PCL) designed for canines.

| Application | For implantation into the capsular bag |
|---|---|
| Optic size optic body | 6.0 mm (60 V-11) |
| | 6.5 mm (60 V-12) |
| | 6.5 mm (60 V-13) |
| | 6.5 mm (60 V-14) |
| Clear optic | 6.0 mm |
| Overall length | 11.0 mm, 12.0 mm, 13.0 mm, 14.0 mm |
| Haptic angulation | 0° |
| Haptic design | Square-edged haptic and optic |
| Optic design | Biconvex |
| Material | Hydrophilic acrylate with 25% water content and UV-blocker |
| Sterilization method | Autoclaving |
| Available diopter | +41.0 D |
| Application | For implantation into the capsular bag |
| Optic size optic body | 6.0 mm (60 V-11) |
| | 6.5 mm (60 V-12) |
| | 6.5 mm (60 V-13) |
| | 6.5 mm (60 V-14) |
| Clear optic | 6.0 mm |
| Optic design | Biconvex |
| Available diopter | +41.0 D |

Occurrence of glaucoma after cataract surgery is especially prevalent in canines, partly because canines tend to experience a substantially higher level of postoperative inflammation subsequent to cataract surgery. The prevalence of the primary breed-related glaucomas has gradually increased from 0.29% (1964-1973); 0.46% (1974-1983); 0.76% (1984-1993); to 0.89% (1994-2002). Breeds that consistently featured among the highest 10 for glaucoma prevalence from four different periods (1964 to 2002) included American Cocker Spaniel, Basset Hound, Wire Fox Terrier, and Boston Terrier. During the last observation period (1994-2002), 22 different breeds had 1% or higher prevalence of the glaucomas. The highest prevalence of glaucomas in 1994-2002 by breed included: American Cocker Spaniel (5.52%); Basset Hound (5.44%); Chow Chow (4.70%); Shar-Pei (4.40%); Boston Terrier (2.88%); Wire Fox Terrier (2.28%); Norwegian ElkHound (1.98%);

Siberian Husky (1.88%); Cairn Terrier (1.82%); and Miniature Poodle (1.68%). A predominance of females with glaucoma occurred in the American Cocker Spaniel, Basset Hound, Cairn Terrier, Chow Chow, English Cocker Spaniel, Samoyed, and perhaps the Siberian Husky, and a predominance of males in the Australian Cattle dog and St Bernard. Age affected the time for first presentation of the glaucoma in the pure-bred dog. In the majority of breeds the glaucoma was presented for initial diagnosis in dogs between 4 and 10 years of age (Gellat, K N, and McKay, E O, "Prevalence of the breed related glaucoma in pure bred dogs in North America", in *Vet Ophthalmol*, 2004; 7(2), pp 97).

In a study of 346 canine eyes, Biros et al. monitored incidence of glaucoma as a function of eight variables, including breed, sex, post-operative hypertension, and intraocular lens placement. Of the 346 canine eyes, 58 (16.8%) developed glaucoma after surgery. At 6 months, 32 of 206 (15.5%) eyes examined had glaucoma; at 12 months, 44 of 153 (28.8%) eyes examined had glaucoma. Median follow-up time was 5.8 months (range, 0.1 to 48 months). Mixed-breed dogs were at a significantly lower risk for glaucoma compared with other breeds. Eyes without IOL placement were at a significantly lower risk for glaucoma compared with eyes with IOL placement. Eyes with hypermature cataracts were at a significantly higher risk for glaucoma, compared with eyes with mature or immature cataracts (Biros et al., "Development of glaucoma after cataract surgery in dogs", in *J Am Vet Med Assoc.*, 2000; 216(11), pp 1780).

Regular and frequent monitoring of intraocular pressure is extremely beneficial during the immediate post-operative period following cataract surgery for humans and canines. In the long run, regular monitoring of intraocular pressure can be used to track the continued efficacy of pressure-controlling medications and monitor compliance with prescribed treatments.

SUMMARY

A sensor that measure intraocular pressure should be encapsulated in a biocompatible coating that acts a barrier between the sensor and the surrounding tissue. Unfortunately, most coatings that act as good barriers prevent the sensor from sensing pressure accurately and from reacting quickly to pressure changes. To address this problem, an inventive implantable pressure sensor's sensing or active surface is coated with a silicone gel, which is hermetically encapsulated with the rest of the sensor in a flexible multi-layer coating. The silicone gel layer provides mechanical protection to the sensor surface while transmitting the pressure of the aqueous without significant damping. It also adheres well to the sensor surface and provides additional protection against incursion of water and water vapor. And the silicone gel layer adheres well to the multilayer hermetic seal, which may be made of alternating layers of Parylene C and $SiO_x$.

An example intraocular lens configured sensing intraocular pressure may include an optic zone, a haptic zone extending from the optic zone, a pressure sensor disposed in or on an anterior side of the haptic zone, a silicone gel layer disposed on a sensing side of the pressure sensor, and a flexible multi-layer coating forming a hermetic seal encapsulating the pressure sensor and the silicone gel layer. In operation, the optic zone, which has a clear aperture with a diameter of at least 6.0 mm, focuses incident light on retina of a mammalian (e.g., human or canine) eye. The haptic zone (e.g., a plate haptic) anchors the intraocular lens within the mammalian eye. The pressure sensor, which does not occluding or obscuring the clear aperture, measures the eye's intraocular pressure. And the silicone gel layer isolates the pressure sensor from tissue of the mammalian eye (and vice versa).

The intraocular lens can be folded along a folding line running parallel to an edge of the pressure sensor and skew to an optical axis of the optic zone. The pressure sensor may comprise at least one of a capacitive sensor or a piezoresistive sensor.

The silicone gel layer may have a bulk modulus of about 0.1 MPA to about 1.0 MPA and a thickness of about 100 microns to about 200 microns. It can be formed of Silastic MDX4-4210 silicone with a 15:1 ratio of base to curing agent. The silicone gel layer may have a concave surface facing away from the sensing side of the pressure sensor.

The flexible multi-layer coating can include at least one ceramic layer and at least one polymer layer. It can have a thickness of about 5 microns to about 50 microns. For instance, it may include alternating layers of Parylene C and SiOx and have a thickness of about 10 microns.

The intraocular lens may also include electronics and at least one battery that are disposed in or on the haptic zone and operably coupled to the pressure sensor and a radio-frequency (RF) coil that is operably coupled to the electronics assembly and disposed about a periphery of the optic zone. In operation, the electronics receive pressure data acquired by the pressure sensor and/or control the pressure sensor. The battery provides electrical power to the pressure sensor and/or the electronics. And the RF coil wirelessly recharges the battery.

More generally, an implantable device may include a pressure sensor with a silicone gel layer with a bulk modulus of about 100 kPA to about 1.0 MPA on the pressure's sensing side and a thickness of 100 microns to 200 microns. For example, the silicone gel layer may include Silastic MDX4-4210 silicone with a 15:1 ratio of base to curing agent. The silicone gel layer may have a concave surface facing away from the sensing side of the pressure sensor.

A flexible multilayer coating forms a hermetic seal encapsulating the silicone gel layer and the pressure sensor, which may be on the anterior side of an intraocular lens. This flexible multilayer coating comprises alternating layers of polymer and ceramic, such as Parylene C and $SiO_x$, respectively, and may have a thickness of about 5 microns to about 50 microns.

An intraocular lens with a plate haptic can be made in part by disposing a pressure sensor on an anterior side of the plate haptic, disposing a soft gel layer on a sensing side of the pressure sensor, and forming a multilayer conformal barrier coating around the soft gel layer and the pressure sensor. Disposing the pressure sensor on the anterior side of the plate optic may include positioning the pressure sensor outside of a clear aperture of an optic of the intraocular lens. The soft gel layer may have a bulk modulus of less than 1.0 MPA and a thickness of about 100 microns to about 200 microns. And forming the multilayer conformal barrier coating may include depositing alternating layers of Parylene C and $SiO_x$ on the soft gel layer.

One aspect of the disclosure is an intraocular lens (IOL), comprising: an optic and a plate haptic configured for four point fixation in the eye, optionally within a capsular sac; and an embedded intraocular pressure (IOP) sensor assembly, wherein the IOP sensor assembly is mounted on a transparent substrate, wherein the substrate is attached to an anterior surface of the IOL, and wherein the optic is wholly or substantially free from obscuration.

One aspect of the disclosure is a method of manufacturing an IOL, comprising: providing an IOL that includes an optic and a plate haptic; positioning an IOP sensor above an anterior side of the plate haptic; optionally positioning a soft gel above the IOL sensor; positioning a multilayer conformal barrier coating above the soft gel; and optionally positioning a biocompatible coating above the barrier coating.

One aspect of the disclosure is a method of folding an IOL for delivery, comprising: providing an IOL that includes an optic and a plate haptic, and a pressure sensor disposed on the plate haptic; and folding the IOL along at least one fold line that is on a first side of the pressure sensor, the fold line not passing through an optical axis of the optic.

One aspect of the disclosure is an intraocular lens, comprising: an optic and at least one plate haptic, and a pressure sensor embedded in the plate haptic.

One aspect of the disclosure is an intraocular lens, comprising: an optic and at least one plate haptic; and an antenna extending around a periphery of the IOL.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally and/or structurally similar elements).

FIGS. 4A-4D illustrate an exemplary plate haptic IOL with an embedded intraocular pressure (IOP) assembly.

FIGS. 4E and 4F show profile and perspective views, respectively, of the plate haptic IOL of FIGS. 4A-4D.

FIG. 8 illustrates an exemplary layering of components for any of the IOLs herein.

FIG. 9A shows a plan view of a foldable IOL with an IOP sensor and two batteries embedded in silicone and encapsulated in flexible hermetically sealed multi-layer coatings.

FIG. 9B shows a profile view along the long edge of the foldable IOL of FIG. 9A.

FIG. 9C shows a profile view along the short edge of the foldable IOL of FIG. 9A in an unfolded configuration.

FIG. 9D shows a profile view along the short edge of the foldable IOL of FIG. 9A in a folded configuration.

FIG. 9F shows material properties for the silicone gel layer covering the pressure sensor in FIG. 9E.

FIG. 11A shows a plan view of a foldable IOL with an IOP sensor and stiffener in one haptic and a battery and PCB in another haptic.

FIG. 11B shows a profile view along the long edge of the foldable IOL of FIG. 11A.

FIG. 11C shows a profile view along the short edge of the foldable IOL of FIG. 11A in an unfolded configuration.

FIG. 11D shows a profile view along the short edge of the foldable IOL of FIG. 11A in a folded configuration.

FIG. 13A illustrates an implantable pressure sensor encapsulated in a silicone with a concave outer surface.

FIG. 13B illustrates an implantable pressure sensor encapsulated in a silicone with a convex outer surface.

DETAILED DESCRIPTION

An implantable pressure sensor can be used in an intraocular lens (IOL) to measure intraocular pressure (IOP) for monitoring glaucoma, recovery from cataract surgery, efficacy of pressuring-controlling medications, or compliance with prescribed treatments in a human or canine. An implantable pressure sensor can be attached to or embedded in the lens portion of an IOL or in one of the haptics that extends from the IOL to anchor the IOL inside the eye.

Placing the implantable pressure sensor in or on the haptic prevents the sensor from occluding the patient's vision or significantly affecting the optical performance or stability of the IOL in the eye.

An implantable pressure sensor can include a capacitive sensor or piezoresistive device that is part of a sensor assembly including electronics used to operate the sensor, including, without limitation a microcontroller, voltage amplifiers, resistors and capacitors, memory units, RFID modules, batteries, and so on. The implantable pressure sensor can be packaged separately from the other electronics, e.g., as a discrete surface-mount component, or integrated with some or all of the other electronics on die (i.e., fabricated on the same semiconductor substrate as the rest of the electronic components).

As mentioned above, an implantable pressure sensor can be embedded in or mounted on an IOL, which may be designed for implantation in the posterior chamber of a mammalian eye. Attaching an implantable pressure sensor to the body of an IOL has several advantages relative to commonly prescribed sites of fixation of such a sensor in intraocular space, for example, in the sclera (making it an intrascleral implant), in the subconjunctival space, the superchoroidal region, the vitreous, or in or near the Schlemms canal. An advantage of embedding a pressure sensor in an IOL is that the sensor is safely away from ocular tissue that may be otherwise disrupted by touch of the sensor body, for example, the iris or the corneal endothelium.

If the pressure sensor is embedded on the anterior side of the IOL, and the IOL is placed in the capsular sac, the pressure sensor is covered by the anterior capsule, which isolates the pressure sensor and protects it from cellular deposits and growth. At the same time, the pressure sensor is surrounded by flowing aqueous humor so that the pressure recorded by the pressure sensor is the true intraocular pressure. Pressure sensors embedded in the sclera, the vitreous, or the subconjunctival space do not measure the pressure of the free flowing aqueous humor. Rather, they measure the pressure of ocular tissue in mechanical contact with the aqueous humor. The sensed pressure for those devices is therefore dampened by the modulus and the viscoelastic properties of the ocular tissue that surrounds the sensor.

IOLs with Pressure Sensors and Electronics on Rigid Substrates

Figure 1:
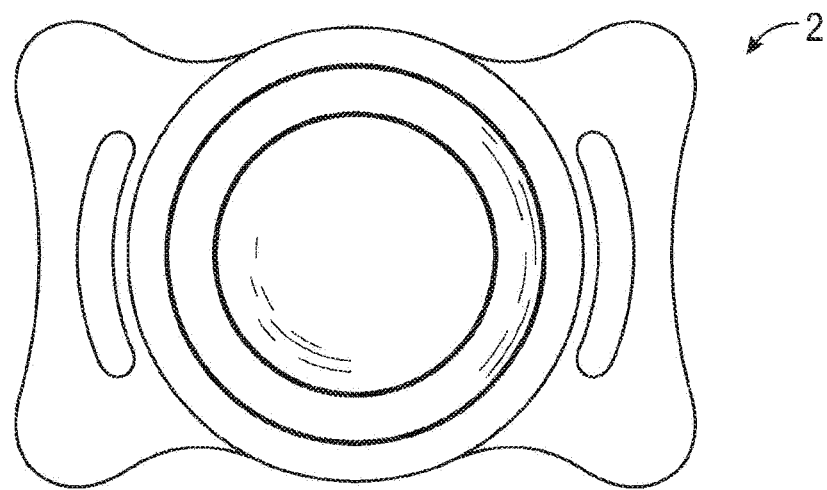
FIG. 1 illustrates an exemplary intraocular lens (IOL) developed for implantation in canines.
Figure 2:
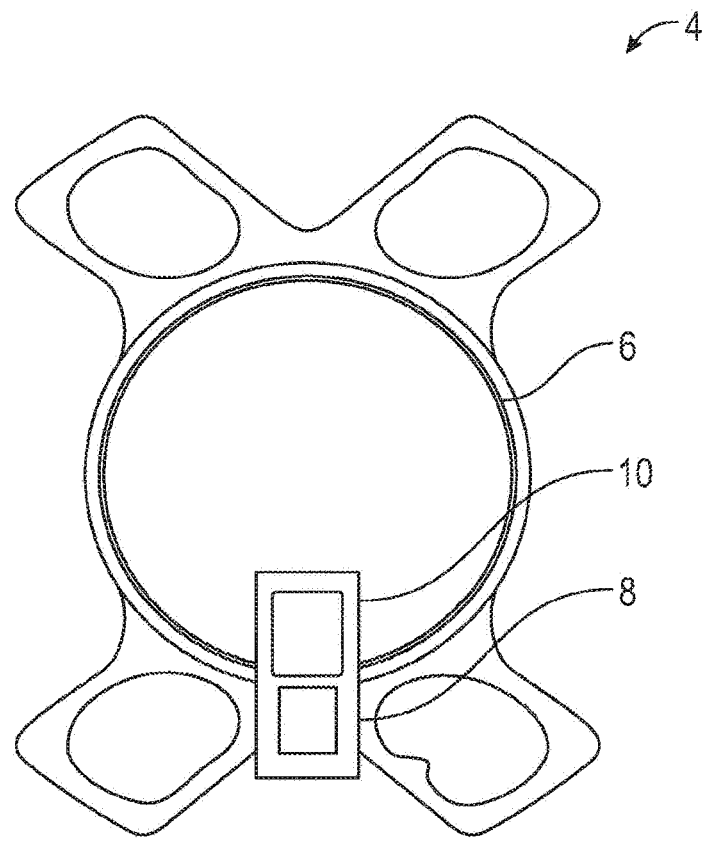
FIG. 2 illustrates an earlier exemplary IOL with an attached sensor.
Figures 3A, 3B:
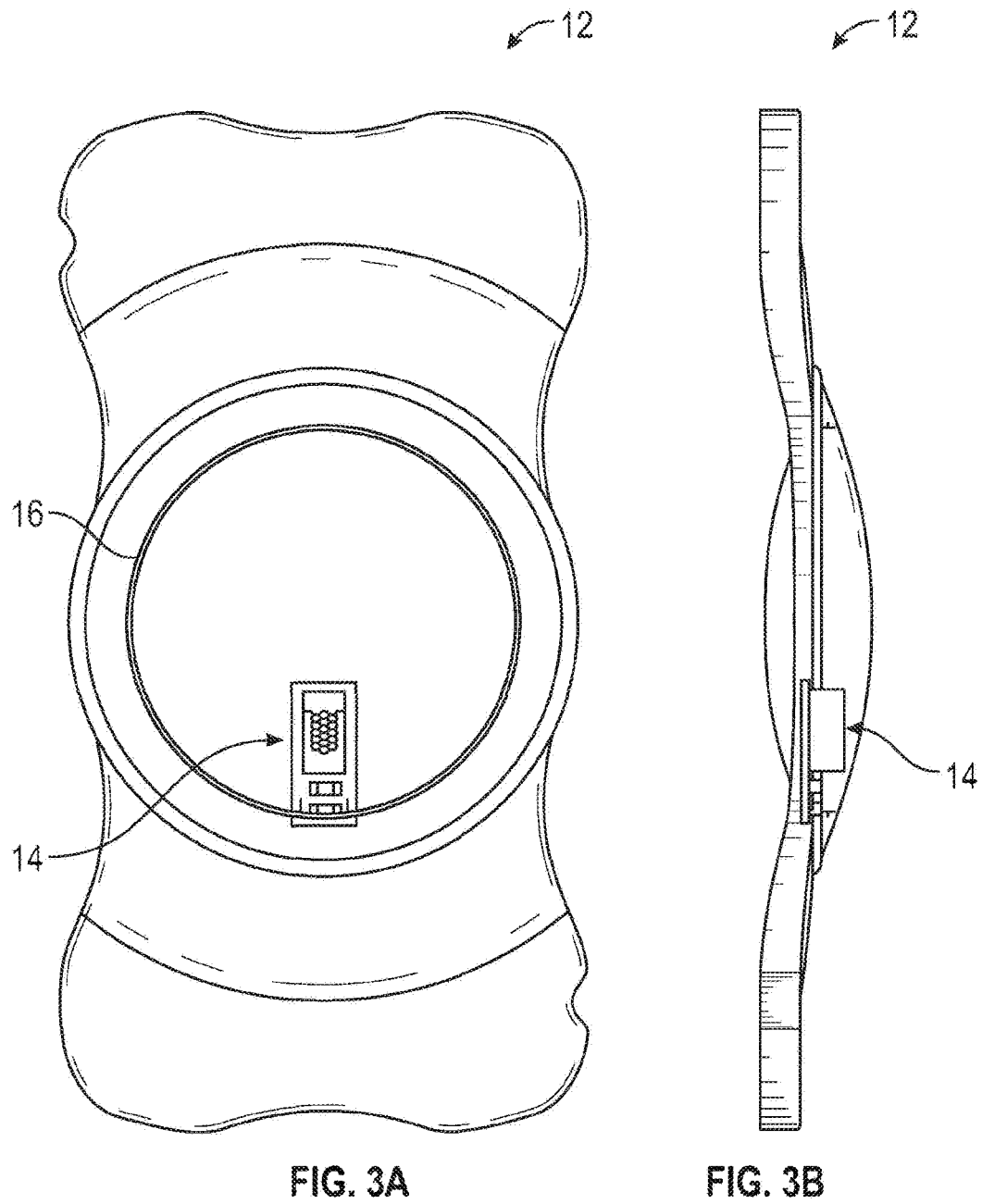
FIGS. 3A and 3B illustrate an earlier exemplary IOL with an attached sensor.

FIGS. 2, 3A, and 3B show conventional IOLs with attached pressure sensors suitable for use in humans or dogs. FIG. 2 shows an IOL 4 with an intraocular pressure sensor 10 mounted on its surface. The pressure sensor 10 extends into the optic zone of the IOL 4 (the portion of the IOL's optic that focuses light) and may occlude at least a portion of the patient's vision. The pressure sensor 10 is coupled to electronics 8 that power and control the pressure sensor 10. These electronics 8 are also coupled to an antenna 6, which can be made of copper or a gold-titanium alloy, coated with gold. The antenna 6 is mounted around the periphery of the IOL's optic zone as shown FIG. 2.

FIGS. 3A and 3B show plan and profile views, respectively, of a canine posterior chamber IOL 12 with an intraocular pressure sensor assembly 14 positioned on its anterior surface. Again, the pressure sensor assembly 14 extends into a portion of the optic zone of the IOL 12. An antenna 16 coupled to the intraocular pressure sensor assembly 14 extends around the periphery of the optic zone of the IOL 14. This IOL 14 may have an optic zone diameter of 6 mm and an overall length of 14 mm.

The IOLs in FIGS. 2, 3A, and 3B are compact and functional because they have a clear central optic zone of 3 mm or larger in diameter. At the same time, the sensors and electronics in these IOLs do obscure part of the IOL optic zone, thereby compromising peripheral vision.

A Pressure-Sensing IOL with a Clear Optic Zone

FIGS. 4A-4F illustrate a plate haptic IOL 40 with an embedded intraocular pressure assembly that does not obscure the IOL's optic zone 42. FIGS. 4A, 4B, 4C, and 4D are top, side, front, and perspective views of the plate haptic IOL 40. The plate haptic IOL 40 is adapted to be foldable, with folding lines shown as the two dashed lines running through FIGS. 4A and 4B and the IOL 40 in a folded configuration in FIGS. 4E and 4F. The folding lines run parallel to the long edge of the IOL and are skew with respect to (i.e., neither parallel to nor intersecting with) the IOL's optical axis, which extends perpendicular to the center of the optic zone 42 and out of the plane of FIG. 4A.

The IOL 40 includes an optic zone or optic portion 42 and plate haptic portion 44. The optic zone 42 may be curved or have a graded refractive index to provide optical power for focusing incident light onto the retina when in a mammalian eye. The IOL 40 also includes an intraocular pressure sensor assembly that includes a pressure sensor module 46 and electronics module 48, which are in electrical communication with each other via electrical connectors 52.

The IOL 40 also includes an antenna 50, which extends around the periphery of the IOL 40, and is in electrical communication with connectors 52. Exemplary dimensions between the folding lines and sensor module 46 are 0.1 mm to 0.6 mm (e.g., 0.2 mm to 0.45 mm, or 0.35 mm). The overall length of the loop antenna 50 can be in the range of 20.0 mm to 30.0 mm (e.g., in the range 22.0 mm to 26.0 mm). The antenna 50 can be made of a wire, for example, of a diameter in a range of 25-200 microns (e.g., 100 microns), and can be mounted on the anterior surface of the IOL 40. Alternatively, the antenna 50 can be comprised of a thin plate of gold or Nitinol coated with gold, of thickness in the range of 10-50 microns and width in the range of 100-250 microns. An advantage of utilizing Nitinol in the antenna 50 is that Nitinol improves the unfolding characteristics of the haptic 44 subsequent to implantation of IOL 40 through a small incision in the eye.

As can be seen in the side views in FIGS. 4A-4D, the sensor module 46 and electronics module 46 are embedded in the plate haptic portion 44 of the IOL 40. The modules 46 and 48 are embedded in or affixed to the upper and lower parts of the plate haptic portion 44 rather than the optic zone 42, ensuring that the optic zone 42 remains clear. The patient's field of view, including their peripheral vision, remains clearer because the modules 46 and 48 do not extend into the optic zone 42. Put differently, the optic zone 42 of the IOL 40 is wholly or substantially free from obscuration. Although there may be some obscuration in the most peripheral region of the optic zone 42, 90%, 95%, 96%, 97%, 98%, 99%, or more of the optic zone's surface area can be free of obscuration. For example, in FIGS. 4A-4C, antenna 50 may extend slightly over the optic zone of the optic, but not significantly enough to occlude or obscure vision.

Flexible, Transparent Coatings and/or Substrates for Implantable Pressure Sensors Another way of providing unobscured peripheral vision is by using a state-of-the-art microelectromechanical assembly with a flexible, transparent substrate. These flexible, transparent substrates can be positioned in or on the haptic of an IOL as in the IOL 40 of FIGS. 4A-4F to further reduce occlusion or obscuration of the patient's peripheral vision.

Figure 5:
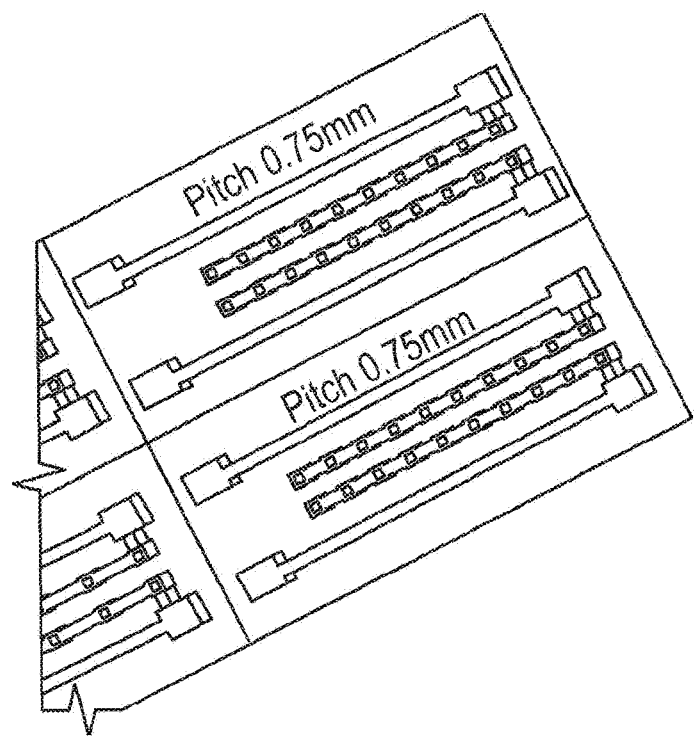
FIG. 5 illustrates an exemplary rigid printed circuit board (PCB).

FIG. 5 shows a rigid, transparent printed circuit board (PCB) that can be used in an IOL to reduce occlusion or obscuration. The rigid, transparent PCB of FIG. 5 can be made of aluminum oxide (Alumina, 99.9%). Exemplary advantages of transparent an Alumina PCB include transparency of up to 80-90%; operating temperature up to 350° C.; low expansion coefficient strong thermal properties (e.g., 26-28 W/mK); multi-layer circuits; hermetic sealing; and 0% water absorption. Other types of transparent PCBs may use polyimide, polyethylene terephthalate, polycarbonate, or glass as substrates.

Figure 6:
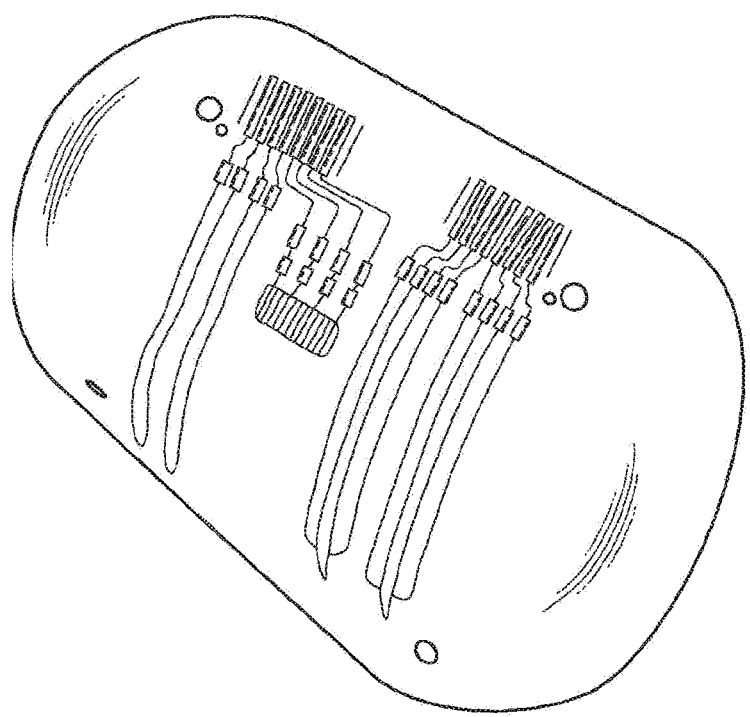
FIG. 6 illustrates an exemplary flexible and transparent PCB.

Unfortunately, the transparent PCB in FIG. 5 is not flexible, which is a useful property for an implantable pressure sensor that may be folded and unfolded during implantation. It is not biocompatible either, nor does it provide isolation from water, ions, and small and large proteins, which are other useful properties for implantable pressure sensors. Fortunately, these properties can be provided by using Parylene C or Graphene as a substrate. FIG. 6 shows a flexible, transparent PCB is developed by COAT-X, located in La Chaux-de-Fonds, Switzerland.

Figure 7:
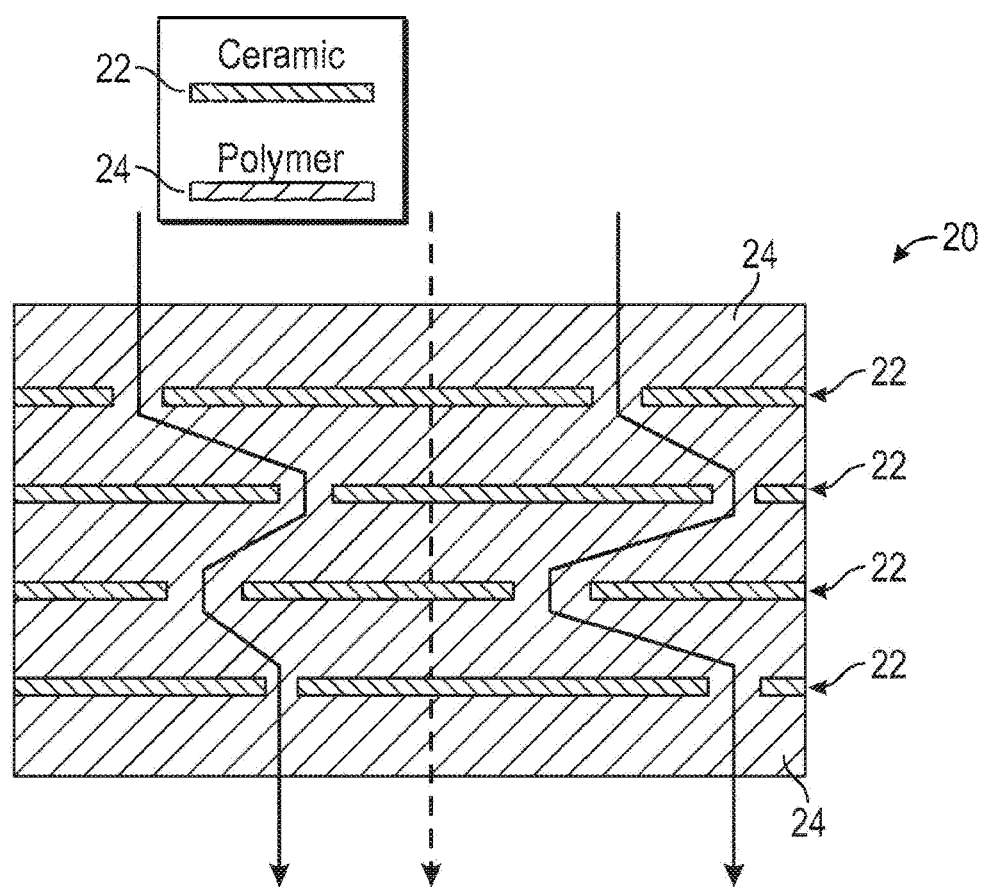
FIG. 7 illustrates details of an exemplary microstructure and layering of a multi-layer film.

The transparent, flexible PCB shown in FIG. 6 includes a substrate made of a multilayer film 20, shown in FIG. 7, comprised of a polymer film 24 with barrier properties, such as Parylene C, interspersed with layers of ceramic 22, such as $SiO_x$, where x is about 1.8 to about 2.0 (e.g., 1.80, 1.85, 1.90, 1.95, or 2.00). In FIG. 7, the ceramic material 22 is shown as the relatively thinner horizontal layers, and the polymeric material 24 is represented as the relatively thicker horizontal layers. The multilayer film 20 can be formed either as a free-standing film or as a conformal coating to provide a hermetic seal around an implant or a portion of an implant, as disclosed in the following patents, incorporated by reference herein for all purposes, including methods of manufacture and methods of application to other materials: U.S. Pat. Nos. 8,313,811; 8,313,819; and 8,361,591. Any and all methods of manufacturing and deposition described in these references are fully incorporated herein and can be used to manufacture any of the flexible components onto the implantable devices disclosed herein. Additional details of the exemplary multilayer ceramic-polymer stack 20 utilizing $SiO_x$ and Parylene C shown in FIG. 7 can be found in A. Hogg et al., "Protective multilayer packaging for long-term implantable medical devices", in Surf. Coat. Technol. (2014), dx.doi.org/10.1016/j.surfcoat.2014.02.070, which is incorporated by reference herein for all purposes.

FIG. 7 shows details of exemplary microstructure and layering of this multi-layer film 20, with arrows illustrating permeation and diffusion. The structure of the film 20 can be used to alter or control the permeation and diffusion. Their effects on the permeation and diffusion properties of these films are discussed in Andreas Hogg's Ph.D. thesis, "Development and Characterization of Ultrathin Layer Packaging for Implantable Medical Devices," which is published on the COAT-X website (coat-x.com/) and is incorporated by reference herein for all purposes.

The antenna 50 and other electrical elements in the IOL 40 of FIGS. 4A-4F may be bonded to a transparent multi-layer film like the one shown in FIG. 7. This film can be bonded to a surface of the IOL 40, preferably the anterior surface. The antenna 50 and the conductive bus 52 may be deposited directly (e.g., via physical or chemical vapor deposition) on the transparent multilayer film. The overall thickness of the multilayer film can be about 10-100 microns (preferably, 20-75 microns).

Soft Encapsulants for Implantable Pressure Sensors with Flexible Coatings

It can be challenging to encapsulate a pressure sensor so that the pressure sensor does not cause any adverse reaction in the body, and in particular in the eye. This is because an encapsulation that provides excellent and durable barrier properties and has a biocompatible surface may isolate the pressure sensor from the hydrostatic and hydrodynamic pressure of the aqueous humor. This isolation may reduce the pressure sensor's sensitivity or responsiveness. It may also introduce an undesirable time lag or latency in sensing pressure changes.

These problems can be addressed by adding a layer of an inert soft elastomer or gel, for example, a soft silicone gel, such as Silastic, available from Dow Corning, or Siluron, available from Geuder Corporation, Germany, then depositing a flexible multilayer coating on top of the soft gel encapsulant. Other suitable materials for this soft gel layer include certain polyurethanes or siloxane substituted epoxies. Tests indicate that this encapsulation package does not materially decrease sensor sensitivity. In fact, tests with a piezoresistive intraocular pressure sensor indicate that the sensor retains greater than 90% of its sensitivity when it is covered by a layer of a silicone (polysiloxane) polymer, then over-coated with a multilayer coating like the coating 20 shown in FIG. 7. For example, the sensitivity of the sensor can be about 1 mbar by itself and can be about 1.2 mbar when encapsulated with the silicone gel and multilayer coating.

But tests indicate that deposition of a material that has a bulk modulus exceeding 1 MPA can adversely affect the response characteristics of the sensor. To avoid these deleterious effects, an inventive implantable pressure sensor may have an elastomeric (e.g., silicone gel) coating whose bulk modulus is about 0.1 MPA to about 1 MPA (e.g., 0.1 MPA, 0.2 MPA, 0.3 MPA, 0.4 MPA, 0.5 MPA, 0.6 MPA, 0.7 MPA, 0.8 MPA, 0.9 MPA, 1 MPA). This silicone gel layer may have a thickness of about 80 microns to about 200 microns (e.g., 100 microns to 200 microns, 80 microns to 120 microns, 80 microns, 85 microns, 90 microns, 95 microns, 100 microns, 105 microns, 110 microns, 115 microns, or 120 microns). A silicone gel layer with a bulk modulus of 1 MPA or less isolates and protects the implantable pressure sensor without unduly degrading the sensor's performance.

FIG. 8 illustrates an exemplary layering of components for an IOL 800 or other substrate with a gel- and film-encapsulated implantable pressure sensor 805. The pressure sensor 850 is disposed above or directly on an anterior side of the IOL 800. A gel layer 832, such as a layer of silicone, is applied above or directly on the sensor 850 or other sensor components. A flexible multilayer barrier coating 831, such as alternating layers of Parylene C and SiOx, can then encapsulate the IOL 800, pressure sensor 850, and gel layer 832. This flexible multilayer barrier coating 831 can be covered in turn by an optional biocompatible coating 801 formulated to reduce inflammation and adhesion of cells to the exposed surfaces.

FIGS. 9A-9D show different views of a foldable plate haptic IOL 900 with a pressure sensor 950, such as a capacitive or piezoresistive pressure sensor, and two batteries embedded in silicone and encapsulated in flexible hermetically sealed multi-layer coatings. This IOL 900 can be used to monitor intraocular pressure in a human or canine eye (and more specifically the pressure of the aqueous humor).

Like the IOL 40 in FIGS. 4A-4F, the IOL 900 in FIGS. 9A-9D has an optic or optic zone 910 that focuses incident light over a diameter of about 6.0 mm to 6.5 mm and a haptic zone 912 (here, in the form of a plate haptic) with portions that extend in opposite directions from the optic zone 910. The IOL 900 includes a processor or electronics assembly 920 embedded in or affixed to one portion of the haptic zone 912 and a sensor assembly 930 embedded in or affixed to one portion of the haptic zone 912. The electronics assembly 920 and sensor assembly 930 are positioned in or on the haptics to avoid occluding or obscuring the user's central and peripheral vision. In other words, they are positioned to keep the optic zone 910 substantially fee of obstructions.

The electronics assembly 920 and sensor assembly 930 are connected to each other via digital lines 906 that run around the periphery of the optic zone 910 and to an RF coil 904 that runs around the periphery of the IOL 900. The electronics assembly 920 includes a processor 922, shown in FIG. 9A as an application-specific integrated circuit (ASIC), that controls the pressure sensor 950 and other electronics. In operation, the pressure sensor 950 acquires data representing the pressure of the aqueous humor; it may also acquire data representing the temperature of the surrounding tissue. The processor 922 receives and transmits the data acquired by the pressure sensor 950 and IOL housekeeping data to an external wireless device, such as an appropriately programmed smartphone, tablet, or laptop, using a near-field communications (NFC) chip 924, radio-frequency identification (RFID) chip, or other suitable wireless transceiver. And it manages wireless re-charging of the batteries with the RF coil 904, which can also be used for wirelessly transmitting data to and receiving commands and data from an external wireless device.

The IOL 900 can be folded along fold lines that run roughly parallel to each other and along the long edges of the electronics assembly 920 and the sensor assembly 930, as shown in FIG. 9D. If the electronics assembly 920 and the sensor assembly 930 are each about 2.00 mm wide and rigid, the total haptic thickness is about 298 microns, and the optic zone thickness is about 650 microns, then the IOL 900 can be folded into a package with a cross-sectional width of about 4.18 mm and a cross-sectional height of about 1.95 mm. This size is limited to some degree by the pressure sensor's dimensions, which may be about 0.5 mm×0.7 mm×1.0 mm. This package can be compressed to an even smaller size for insertion into a small incision in the eye of a person or dog. Once inserted into the eye, the IOL 900 unfolds on its own, possibly due to memory or hysteresis in the RF coil 904. The haptic zone 912 anchors the IOL 900 in the eye (e.g., in the posterior chamber of the eye), enabling the pressure sensor 950 to measure the pressure of the vitreous humor.

Figure 9E:
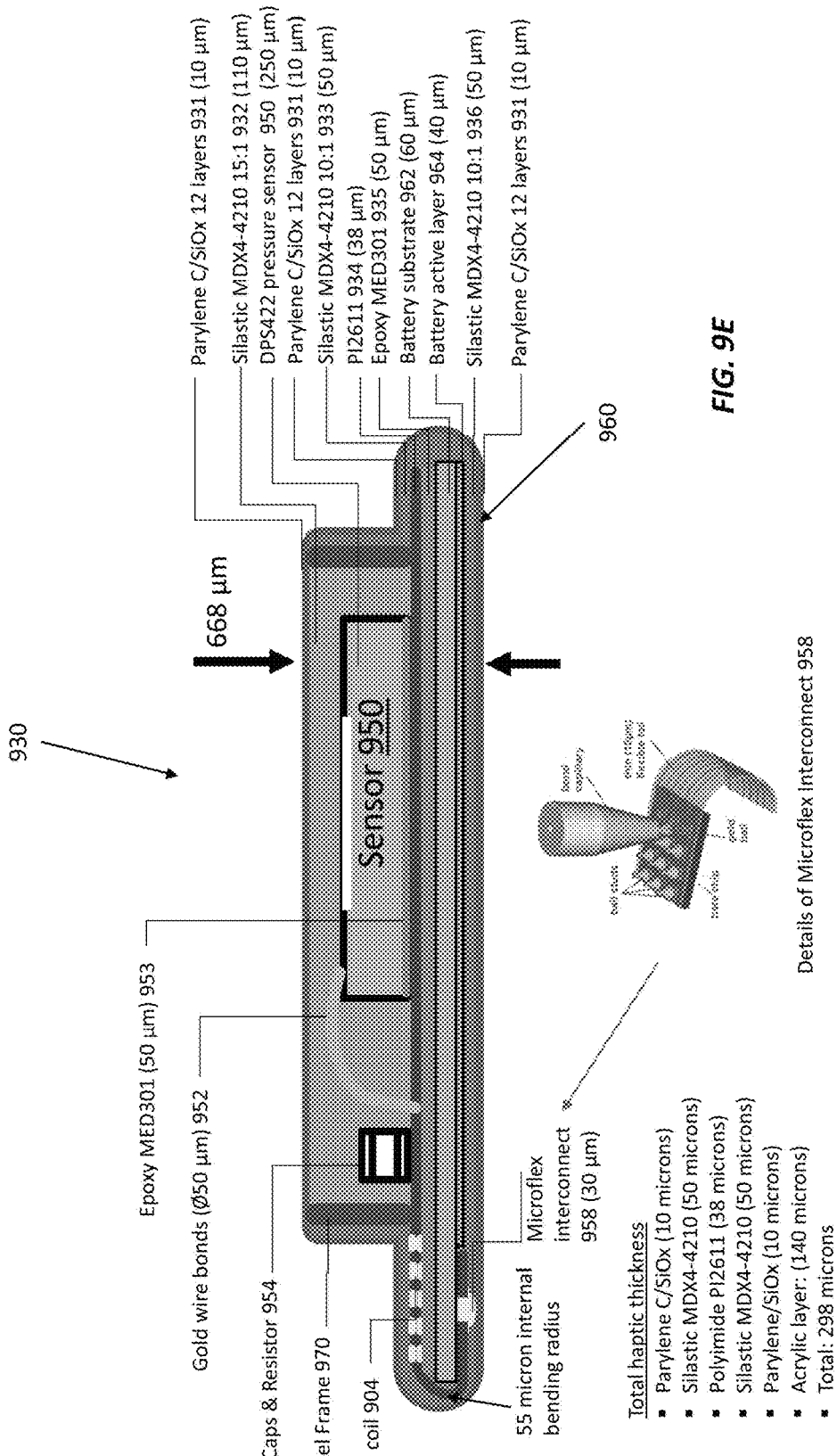
FIG. 9E shows a cross-sectional view of an IOP sensor, battery, silicone, and flexible hermetically sealed multi-layer coating suitable for use in the foldable IOL of FIG. 9A.

FIG. 9E shows a cross-sectional view of the pressure sensor assembly 930. The entire assembly 930 is hermetically sealed in a flexible, biocompatible multilayer coating 931 that may itself be coated in a biocompatible coating (not shown). This flexible, multilayer coating 931 include multiple (e.g., 10 or 12) alternating layers of Parylene C and $SiO_x$, each of which is just under 1 micron thick for a total multilayer coating thickness of about 10 microns. An implantable silicone gel layer 932, such as a 110-micron thick layer of Silastic MDX4-4210 silicone with a 15:1 ratio of base to curing agent, separates the multilayer coating 931 from the upper (active/sensing) side of the pressure sensor 950, which may be an Infineon Technologies DPS422 pressure and temperature sensor with a thickness of 250 μm. This 15:1 ratio of base to curing agent is selected to ensure that the silicone gel layer's bulk modulus is 100 kPA to 1 MPA as explained above. The gel layer 932 is soft, with a hardness of less than or equal to 25 on the Shore A hardness scale. FIG. 9F shows the material properties of Silastic MDX4-4210 silicone and other materials that could be used in the gel layer 932.

Together, the multilayer coating 931 and silicone gel layer 932 protect and isolate the pressure sensor 950 without reducing the pressure sensor's sensitivity or responsiveness. The other side of the pressure sensor 950 sits on a 50-micron-thick layer 953 of implantable-grade epoxy, such as EPO-TEK® MED-301 biocompatible, spectrally transparent epoxy. This epoxy is implantable for more than 30 days, electrically insulating, and has a curing temperature below 85° C. (sensor limitation) and a glass transition temperature over 55° C. (the Silastic silicone curing temperature). Its coefficient of thermal expansion (CTE) is low and to polyimide, ceramic, and glass. When cured, the epoxy's hardness is between Shore 75D and 85D to limit thermally induced stresses at the bonding interface (lower hardness is better). MED-301 epoxy has an uncured viscosity of 100 cPs to 1000 cPs, which facilitates degassing in small gaps of flip chip components and is thixotropic for automatic dispensing. The epoxy layer 953, sensor 950, and gel layer 932 are contained laterally within a cadmium-free stainless steel frame 970 that also contains surface-mounted capacitors and resistors 954.

The pressure sensor 950 is supported by a planar battery 960, which includes a 60-micron-thick battery substrate 962 and a 40-micron-thick battery active layer 964. The pressure sensor 950 connects to the battery substrate 962 via one or more gold wire bonds 952, which may have 50-micron diameters, that couple electrically to the RF coil 904 and/or digital lines 906 (FIG. 9A). The RF coil 904 and digital lines 906 are patterned in or on the plane of a 38-micron-thick polyimide layer 934 (e.g., PI-2611 polyimide), which acts as a PCB, on another 50-micron-thick layer of epoxy 935. The RF coil 904 is electrically coupled to the battery 960 via a microflex interconnect 958 with a 55-micron internal bending radius and 30 micron thickness, shown in detail in the inset at the bottom of FIG. 9E. An implantable-grade silicone layer 936, such as a 50-micron-thick of Silastic MDX4-4210 with 10:1 base-to-curing-agent ratio, surrounds the bottom and sides of the battery 960 and the sides of the steel frame 970. This silicone formulation is highly hydrophobic, picking up less than 0.2% by weight of water at equilibrium, and has an ultralow modulus (e.g., <1 MPA).

The total thickness of the pressure sensor assembly 930, include the surrounding multilayer coating 931, is 668 microns. By comparison, the rest of the haptic zone 912 has a total thickness of 298 microns and includes, in cross section: a flexible multilayer coating of Parylene C and SiOx (10 microns), a layer of Silastic MDX4-4210 silicone (50 microns), a layer PI-2611 polyimide (38 microns), another layer of Silastic MDX4-4210 silicone (50 microns), another flexible multilayer coating of Parylene C and SiOx (10 microns), and an acrylic layer (140 microns).

FIGS. 10A-10F illustrate a foldable IOL 1000 with an IOP sensor and two metallized batteries 1060 and 1080 embedded in silicone and encapsulated in flexible hermetically sealed multi-layer coatings. Like the foldable IOL 900 shown in FIGS. 9A-9D, this IOL 1000 includes a pressure sensor 950 can be used to monitor pressure in the eye of a human or dog. It also includes an RF coil 902, digital lines 904, optic zone 910, haptic zone 912, and/or other components described above with respect to FIGS. 9A-9E. And it can be folded for insertion into a patient's eye along fold lines that run alongside the edges of an electronic assembly 1020 and pressure sensor assembly 1030 embedded in the haptic 912.

Figures 10A, 10B, 10C, 10D:
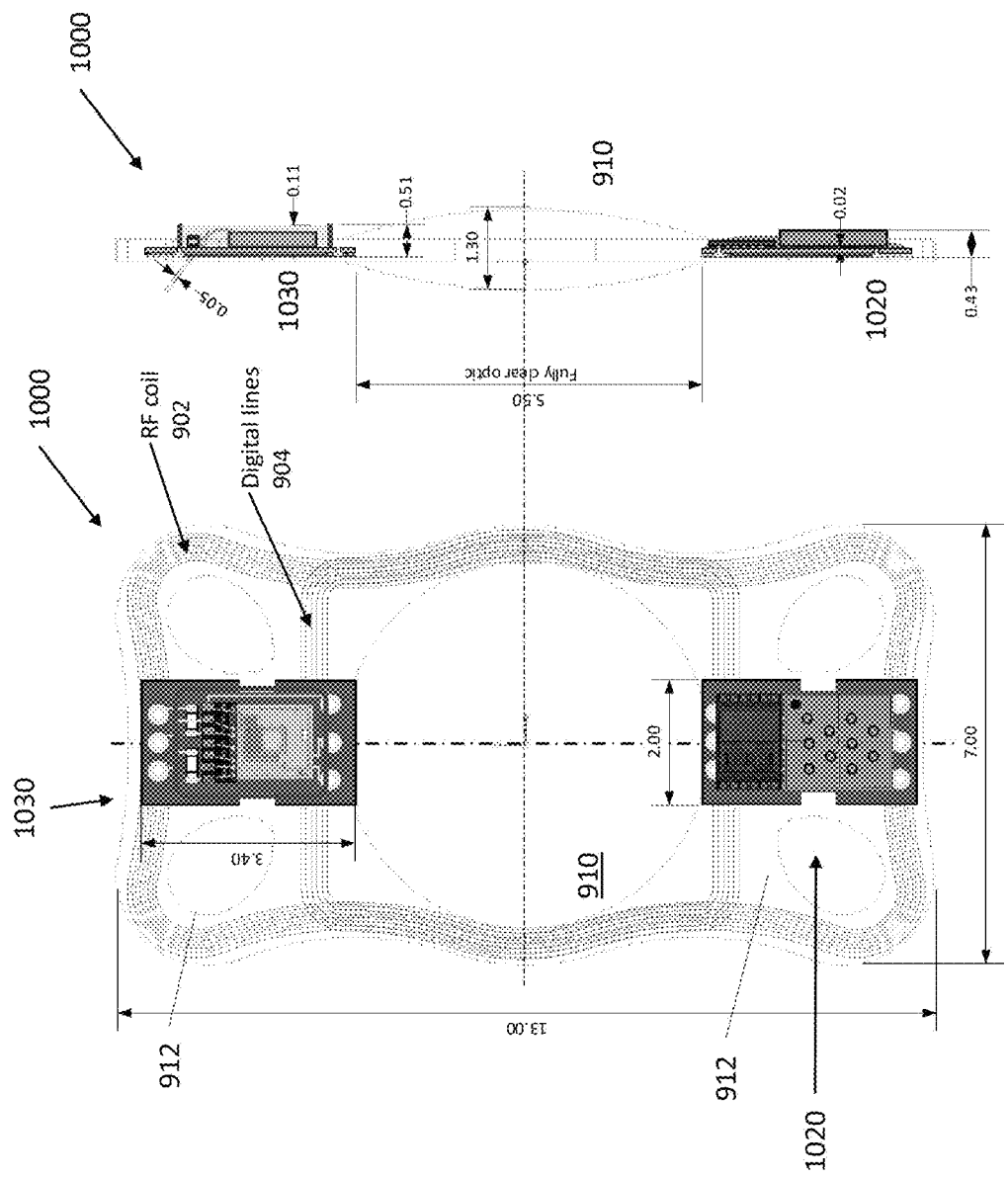
FIG. 10A shows a plan view of a foldable IOL with an IOP sensor and two metallized batteries embedded in silicone and encapsulated in flexible hermetically sealed multi-layer coatings.
FIG. 10B shows a profile view along the long edge of the foldable IOL of FIG. 10A.
FIG. 10C shows a first metallized battery suitable for use in the foldable IOL of FIG. 10A.
FIG. 10D shows a second metallized battery suitable for use in the foldable IOL of FIG. 10A.

FIGS. 10C and 10D show metallized batteries 1060 and 1080, respectively, that are in the electronics assembly 1020 and pressure sensor assembly 1030, respectively. Unlike other batteries, these metallized batteries 1060 and 1080 have metal terminals connected to the pads that connect the batteries to the circuit. These batteries also have vias 1061 for electrical connections and notches 1063 for positioning the stainless steel frame 1030 and other components in these assemblies.

Figure 10E:
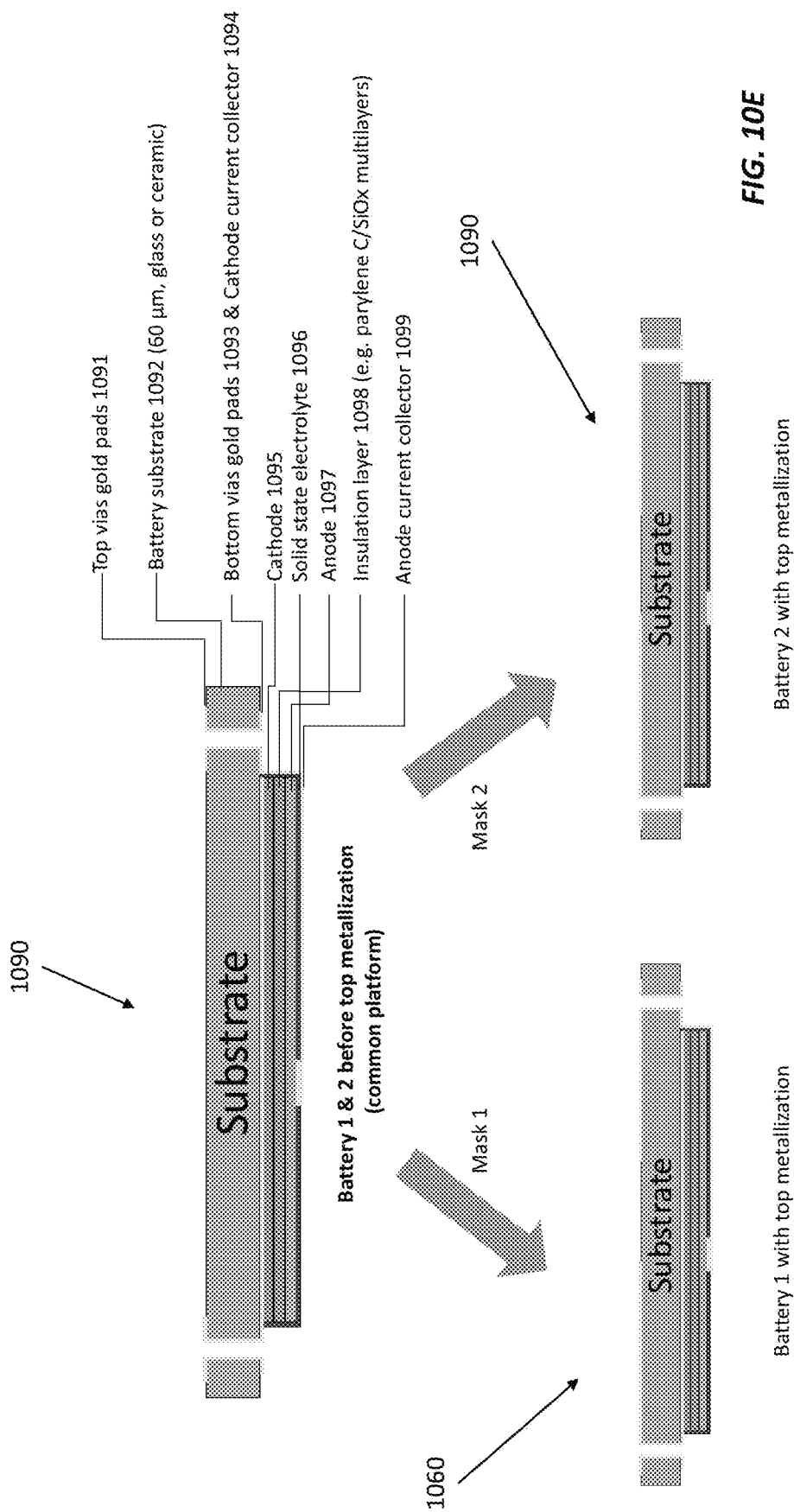
FIG. 10E illustrates fabrication of the metallized batteries in FIGS. 10C and 10D.

FIG. 10E illustrates the layer structure and a process for making these metallized batteries 1060 and 1080. The batteries can start as a common platform 1090 before metallization of its upper surface. This common platform 1090 (and each batter) has a battery substrate 1092 (e.g., a 60-micron-thick glass or ceramic layer) that supports the battery's active layers, which include a cathode current collector 1094, cathode 1095, solid-state electrolyte 1096, anode 1097, insulation layer 1098 (e.g., a stack of Parylene C/$SiO_x$ layers), and anode current collector 1099. Top via gold pads 1091 and bottom via gold pads 1093 provide contacts from electrical connections. The batteries can be metallized using different masks so that they can be coupled to different components (e.g., the pressure sensor 950 and processor).

Figure 10F:
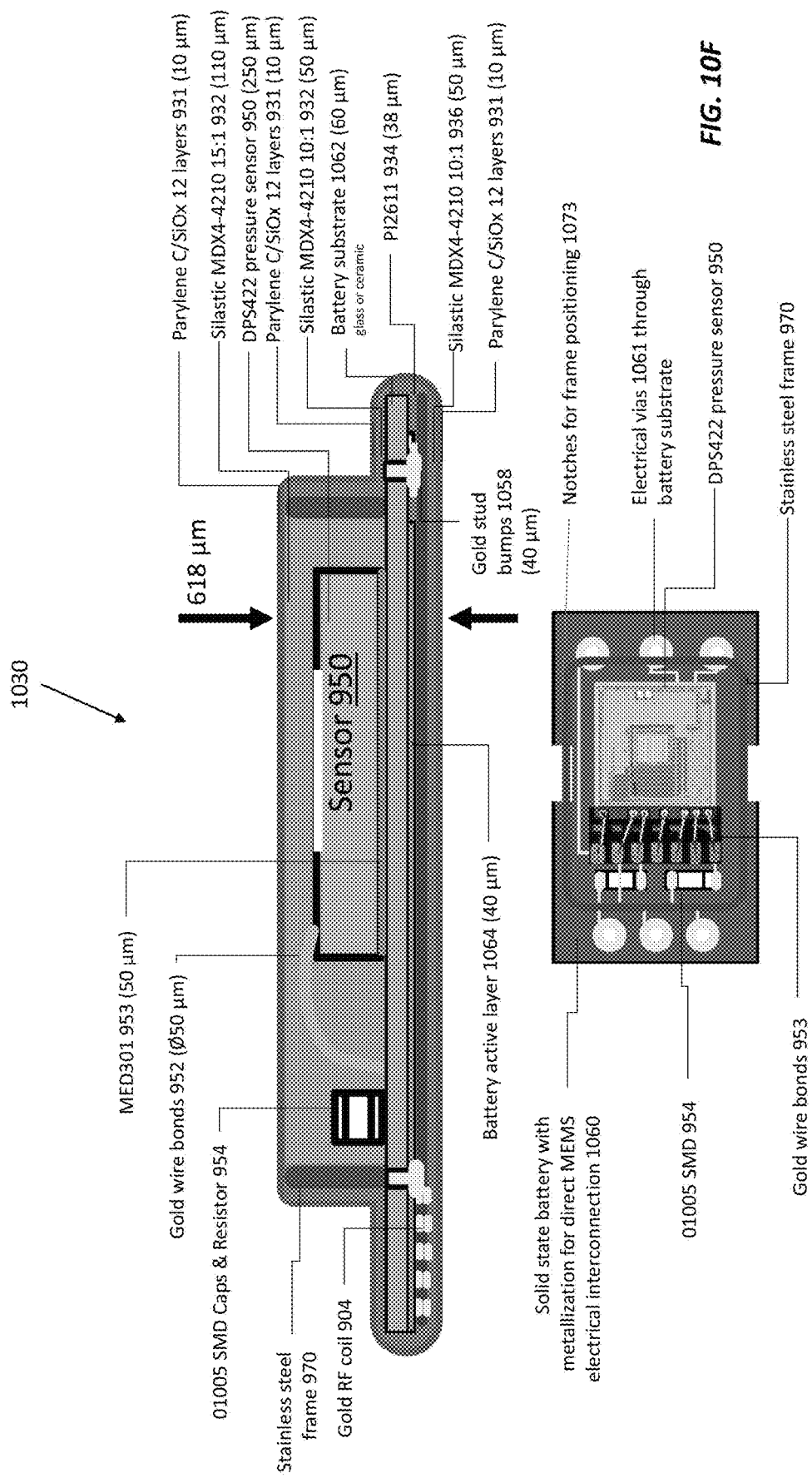
FIG. 10F shows a cross-sectional view of an IOP sensor, metallized battery, silicone, and flexible hermetically sealed multi-layer coating suitable for use in the foldable IOL of FIG. 10A.
Figure 11E:
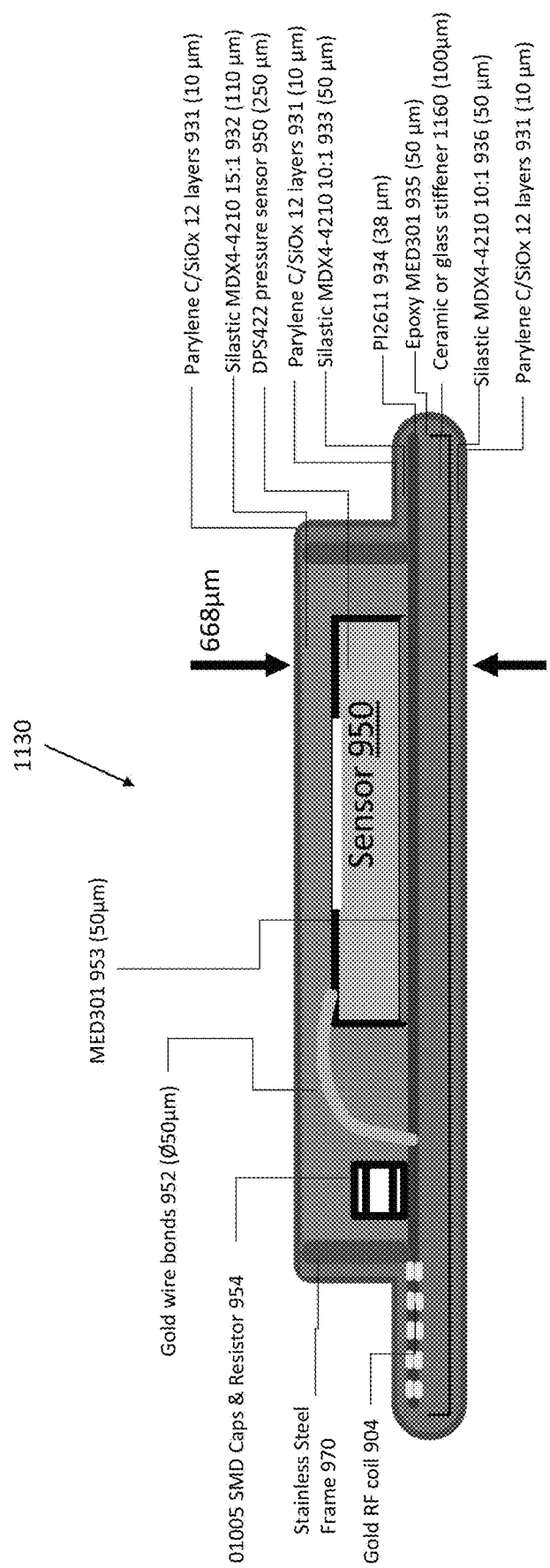
FIG. 11E shows a cross-sectional view of an IOP sensor, stiffener, silicone, and flexible hermetically sealed multi-layer coating suitable for use in the foldable IOL of FIG. 11A.

FIG. 10F shows a cross-sectional view of the pressure sensor assembly 1030. This pressure sensor assembly 1030 is encapsulated in a biocompatible multilayer coating 931 that hermetically seals the components inside pressure sensor assembly 1030 for implantation. A silicone gel layer 932 between the pressure sensor 950 and the multilayer coating 931 further isolates the pressure sensor 950 from the surrounding tissue without unduly degrading the pressure sensor's performance. The multilayer stacking of the electrical components uses on-die manufacturing processes to achieve a smaller form factor due to further miniaturization of the individual components.

FIGS. 11A-11E illustrate a foldable IOL 1100 with a pressure sensor assembly 1130 in one part of the haptic zone 912 and a battery and PCB assembly 1120 in another part of the haptic zone 912. Like the foldable IOL 900 shown in FIGS. 9A-9D, this IOL 1100 includes a pressure sensor 950 can be used to monitor pressure in the eye of a human or dog. It also includes an RF coil 902, digital lines 904, optic zone 910, haptic zone 912, and/or other components described above with respect to FIGS. 9A-9E.

FIG. 11A also shows folding lines 1111, with FIG. 11D showing a profile view of the IOL 1100 in a folded state. These folding lines 1111 are parallel to each other and in a plane that is orthogonal to the IOL's optical axis. In this case, the pressure sensor 950 is on a glass or ceramic stiffener 1160 with a thickness of about 100 microns instead of a battery as in the IOLs described above. To make up for this missing battery, the pressure sensor assembly 1130 may draw electrical power from the battery in the battery and PCB assembly 1120 via digital lines 904. Alternatively, the pressure sensor assembly may include a battery, and the electronics assembly may include a glass or ceramic stiffener instead of a battery and may draw electrical power from the battery in the pressure sensor assembly.

Figures 12A, 12B, 12C:
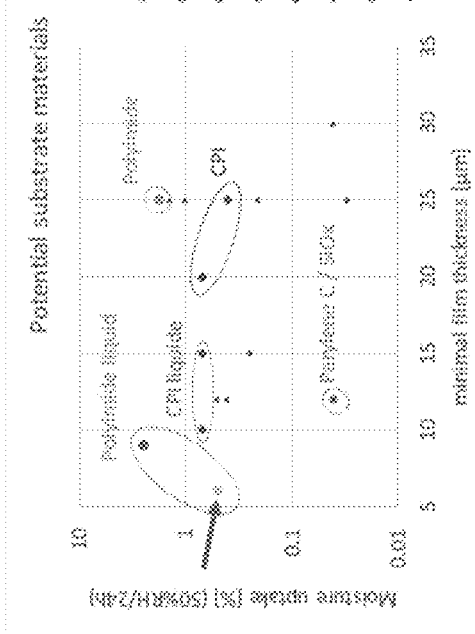
FIG. 12A is a plot of moisture uptake versus minimal film thickness for different IOL substrate materials.
FIG. 12B is a plot of rigidity versus coefficient of thermal expansion (CTE) for different IOL substrate materials.
FIG. 12C is a table showing specifications for a layer of cured PI-2611 polyimide.

FIGS. 12A-12C illustrate characteristics of substrate materials for mounting of electronic components. FIG. 12A is a plot of moisture uptake versus minimal film thickness for different IOL materials and material combinations, including multilayer Parylene C/$SiO_x$ coatings and polyimide. FIG. 12B is a plot of rigidity versus coefficient of thermal expansion (CTE) for the same IOL materials and material combinations. And FIG. 12C is a table showing specifications for a layer of cured PI-2611 polyimide. These figures show that PI-2611 polyimide has low water absorption (~0.5%) and a low dielectric constant leading to lower dielectric loss than other substrate materials.

FIGS. 13A and 13B illustrate the effect of adding a layer of a soft silicone elastomer (e.g., silicone gel layer 932 in FIGS. 9E, 10F, and 11E) on top of a pressure sensor. The vulcanization (cross-linking) of the silicone gel layer 932 causes very little change in its molar volume (e.g., about 0.2%), but this volume change may cause a slight concave curvature to develop over the sensor surface as shown in FIG. 13A. This concave gel surface over the sensor 950 may induce a negative pressure offset in the pressure sensor reading. Conversely, a convex gel surface like the one shown in FIG. 13B may induce a positive offset in the pressure sensor reading. Generally, a negative offset is preferred since the work range of the sensor is from 300 mbars to 1200 mbars, while ambient pressure is close to 800 mbars. The sensor offset can be measured at each step of the encapsulation process, especially before and after gel vulcanization.

Figure 13C:
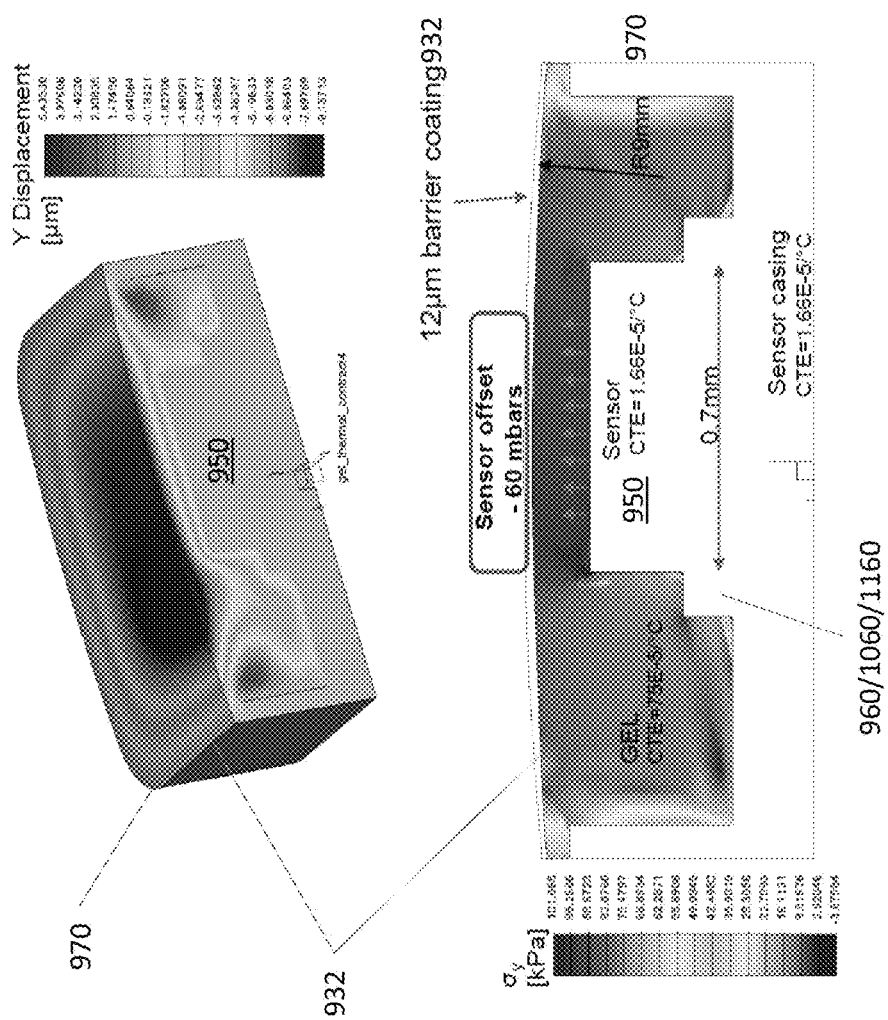
FIG. 13C illustrates finite element (FE) simulations of an implantable pressure sensor encapsulated in a silicone experiencing a temperature drop during deposition of a multi-layer coating.

FIG. 13C illustrates a finite element (FE) analysis of silicone gel layer on a pressure sensor subject to a temperature drop from about 50° C. to about 25° C., with an average gel pressure on the sensor during the temperature drop of about 60 mbars. The silicone gel layer may experience this temperature drop during application of the multilayer coating. This temperature drop causes the silicone gel layer to contract, changing the shape of the surface of the silicone gel layer that faces away from the pressure sensor (e.g., from flat to convex or concave) and possibly induces a negative sensor offset. Subject the silicone gel layer to vacuum pressure during application of the multilayer coating may also induce a negative sensor offset.

Figure 14:
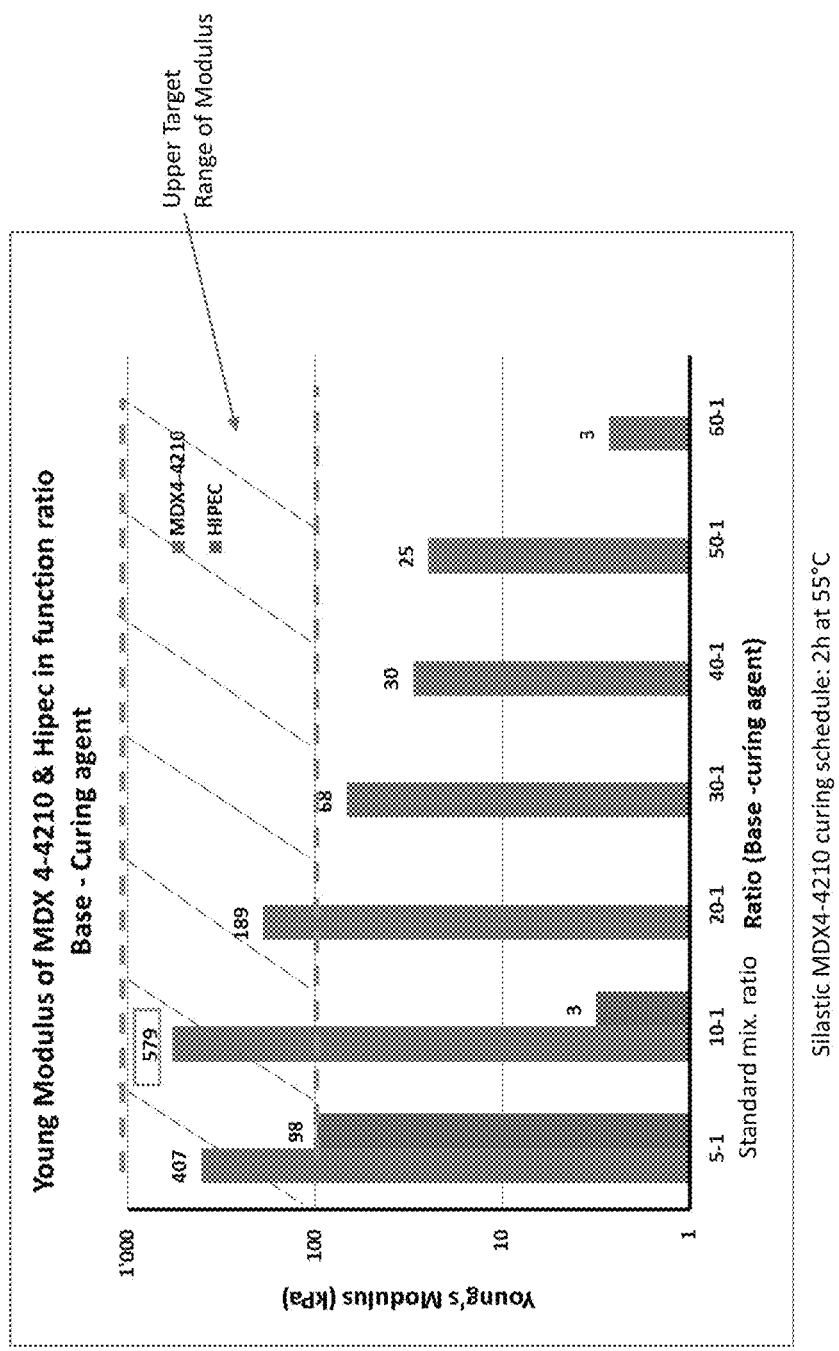
FIG. 14 is a bar chart showing the Young's moduli of Silastic® MDX 4-4210 biomedical elastomer and HIPEC™ semiconductor coating at different ratios of base to curing agent.

FIG. 14 is a bar chart showing the Young's moduli of Silastic® MDX 4-4210 biomedical elastomer and HIPEC™ semiconductor coating at different ratios of base to curing agent. Young's modulus describes tensile elasticity, or the tendency of an object to deform along an axis when opposing forces are applied along that axis. It is defined as the ratio of tensile stress to tensile strain. The bulk modulus describes volumetric elasticity, or the tendency of an object to deform in all directions when loaded uniformly in all direction. It is defined as the ratio of volumetric stress to volumetric strain and can be considered an extension of Young's modulus in three dimensions. The bulk modulus scales linearly with Young's modulus.

FIG. 14 shows that increasing the ratio of base to curing agent reduces the Young's modulus and, by extension, the bulk modulus. The preferred range of Young's modulus for the silicone gel layer (e.g., layer 932 in FIG. 9E) provides a balance between transmission of mechanical impulses from the aqueous humor to the pressure sensor, and a cushioning effect for the pressure sensor. As shown in FIG. 14, this range is about 100 kPA to about 1000 kPA (1 MPA). MDX4-4210 silicone has a Young's modulus of about 100 kPA to about 1000 kPA for a base:curing-agent ratio of 5:1 to almost 30:1 (e.g., 15:1 or 20:1). HIPEC™ semiconductor coating has a Young's modulus of about 100 kPA to about 1000 kPA for a base:curing-agent ratio of about 5:1.

CONCLUSION

An implant comprising an intraocular pressure sensor, coated with a multilayer coating like the one shown in FIG.

7, can be coated with an organic biocompatible coating that reduces adhesion of cells to the implant. For an IOL, the biocompatible coating may reduce adhesion of cortical and endothelial cells. These cells that are remnants of the crystalline lens that is removed prior to implantation of the IOL. Preferably, this biocompatible coating reduces or minimizes stimulation of the inflammation cascade in the implantation site (e.g., the eye).

The biocompatible coating can be a multilayer amphiphilic or hydrophilic coating, with a gradation of cross-link density, glass transition temperature and bulk modulus. It can be made of a hydrogel material and may comprise two or more layers. The inner layer(s) of this biocompatible coating can be infused with pharmaceuticals, such as an anticlotting agent, antifibrotic agent, corticosteroid, and/or other medicaments that downregulate expression of inflammation mediators, such as cytokines. The multilayer coating, similar in molecular structure to an extracellular matrix, prevents adhesion of giant cells, or polymorphic macrophage. For example, its microstructure can be that of a scaffold, with an inner layer with the highest cross-link density and an outer layer of lowest cross-link density. The biocompatible coating can be applied via photopolymerization and comprises polyethylene glycol segments terminated with acrylate or methacrylate groups.

The plate haptic IOLs disclosed herein (e.g., in FIGS. 4A-4F, 9A-9D, 10A, 10B, -) can be configured to engage the capsular equator at four points and is therefore quite resistant to rotational displacement. They may not be vaulted, but a vault of up to 7 degrees is acceptable. A vault further separates the intraocular sensor assembly from the iris. The overall length of the IOL can be between 11.5 and 12.7 mm, e.g., 12.5 mm. In FIG. 4A, for example, the IOL's length is shown as 12.3 mm. The IOL can be implanted in a folded state, e.g., along lines bordering (on at least one side of) the electronic modules and the sensor module, such as is shown in FIGS. 4A, 4B, 4E, and 4F. Such a folding pattern enables the IOL 40 to be delivered through a 3.3 mm incision. The haptic portions of the IOL can also be adapted to be more preferential to folding along the folding lines to facilitate folding in particular areas on both sides of the electronics modules and the sensor module.

One advantage of the IOLs disclosed herein over other IOLs is that they provide a full diameter optic that can be up to 6.0 mm in diameter. Alternative designs may be provided that have an optic zone with a diameter from 5.0 mm to 6.5 mm, and an outer diameter of 6.0 to 7.5 mm. A second advantage is that the IOLs herein accommodate an antenna of total length in the range of 20.0 to 25.0 mm, more than three time the length provided by previous designs.

The edge of a plate haptic IOL can be designed to have a square profile. Since the edge of the optic has a thickness in the range of 50-150 microns, the overall thickness of the edge bearing the antenna coil can be in the range of 150-525 microns (e.g., 200-400 microns). This increase in edge thickness and a barrier on the anterior surface of the IOL may reduce or eliminate migration of residual cortical and equatorial cells left over after phacoemulsification and cleaning of the capsular sac prior to lens implantation to the posterior capsule, and thus helps inhibit posterior capsular opacification (PCO).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An implantable device, comprising:
a pressure sensor for acquiring and measuring pressure;
a silicone gel layer, disposed on a sensing side of the pressure sensor, to isolate the pressure sensor from tissue surrounding the implantable device;
a flexible multilayer coating forming a hermetic seal encapsulating the pressure sensor and the silicone gel layer, the flexible multilayer coating comprising alternating layers of polymer and ceramic;
an electronics assembly operably connected to the pressure sensor and configured to receive pressure data acquired by the pressure sensor; and
an antenna operably connected to the electronics assembly,
wherein the silicone gel layer has a bulk modulus of about 0.1 MPA to about 1.0 MPA, a 15:1 ratio of base to curing agent, and a thickness of about 100 microns to about 200 microns,
wherein the polymer in the flexible multilayer coating comprises Parylene C, the ceramic in the flexible multilayer coating comprises SiOx, and the flexible multilayer coating has a thickness of about 5 microns to about 50 microns.

2. The implantable device of claim 1, wherein the implantable device comprises an intraocular lens and the pressure sensor is disposed on an anterior side of the intraocular lens.

3. The implantable device of claim 1, wherein the silicone gel layer forms a concave surface facing away from the sensing side of the pressure sensor.

4. The implantable device of claim 1, wherein the silicone gel layer comprises Silastic MDX4-4210 silicone.

5. The implantable device of claim 1, wherein the flexible multilayer coating has a thickness of about 10 microns.

6. The implantable device of claim 1, wherein x is about 1.8 to about 2.0.

7. The implantable device of claim 1, wherein the flexible multilayer coating comprises 10 alternating layers of polymer and ceramic.

8. The implantable device of claim 1, wherein the flexible multilayer coating comprises 12 alternating layers of polymer and ceramic.

9. The implantable device of claim 1, wherein the flexible multilayer coating is disposed on the silicone gel layer.

10. The implantable device of claim 1, wherein the electronics assembly comprises an application-specific integrated circuit (ASIC).

11. The implantable device of claim 1, further comprising a battery configured to provide power to the pressure sensor.

* * * * *